United States Patent [19]

Kraus et al.

[11] Patent Number: 5,273,052
[45] Date of Patent: Dec. 28, 1993

[54] GUIDEWIRE WITH REVERSIBLE CONTACT SEAL FOR RELEASABLE SECUREMENT TO CATHETER

[75] Inventors: Jeff L. Kraus, San Jose; John W. Danforth, San Francisco; Michael J. Horzewski, San Jose, all of Calif.

[73] Assignee: Danforth Biomedical, Incorporated, Menlo Park, Calif.

[21] Appl. No.: 817,939

[22] Filed: Jan. 8, 1992

[51] Int. Cl.$^5$ ............................................. A61M 25/00
[52] U.S. Cl. ...................................... 128/772; 604/95; 604/96
[58] Field of Search ............................ 128/656-658, 128/772; 606/192, 194; 604/96, 107, 95, 249, 264, 280

[56] References Cited

U.S. PATENT DOCUMENTS

| | | | |
|---|---|---|---|
| 3,978,863 | 9/1976 | Fettel et al. | 128/348 |
| 4,655,746 | 4/1987 | Daniels et al. | 604/53 |
| 4,932,959 | 6/1990 | Horzewski et al. | 606/194 |
| 5,045,061 | 9/1991 | Seifert et al. | 604/96 |
| 5,178,608 | 1/1993 | Winters | 604/99 |

FOREIGN PATENT DOCUMENTS

| | | |
|---|---|---|
| WO84/01903 | 5/1984 | PCT Int'l Appl. |
| WO86/06285 | 11/1986 | PCT Int'l Appl. |
| WO88/00844 | 2/1988 | PCT Int'l Appl. |
| WO91/04763 | 4/1991 | PCT Int'l Appl. |
| WO92/08511 | 5/1992 | PCT Int'l Appl. |

OTHER PUBLICATIONS

EPO Search Report, Document No. 93300062.2, dated May 4, 1993.

Primary Examiner—C. Fred Rosenbaum
Assistant Examiner—Corrine Maglione
Attorney, Agent, or Firm—Townsend and Townsend Khourie and Crew

[57] ABSTRACT

An exchangeable catheter-guidewire system is disclosed in which the guidewire can be manipulated to seize and to release itself from the catheter body while both are in place in a vasculature or other body vessel. For balloon dilatation catheters, this arrangement permits one to transmit the fluid used for perfusion and/or balloon inflation through the same lumen through which the guidewire passes. Balloon catheters which utilize the invention have the capacity to secure the position of the guidewire relative to the catheter body, as well as to seal the lumen and balloon to retain fluid under pressure, both by remote control from the proximal end of the catheter. The seizure and sealing are achieved by a deformable section on the guidewire, which expands upon deformation to seize a tubular section of the catheter body. Two examples of deformation are given, the first occurring with a deformable section which is sufficiently flexible to gather into folds upon longitudinal compression, the folds being bulky enough to expand outward, and the second occurring with a deformable section which is inflatable. In either case, the guidewire in preferred embodiments is constructed as a hollow tube with a central rod which in both cases serves to enhance the longitudinal strength of the guidewire and, in the first case, also serves as a means of compressing and re-extending the deformable section of the tube. Either mechanism permits the construction of an exchangeable catheter system with the crossing profile of non-exchangeable systems.

30 Claims, 10 Drawing Sheets

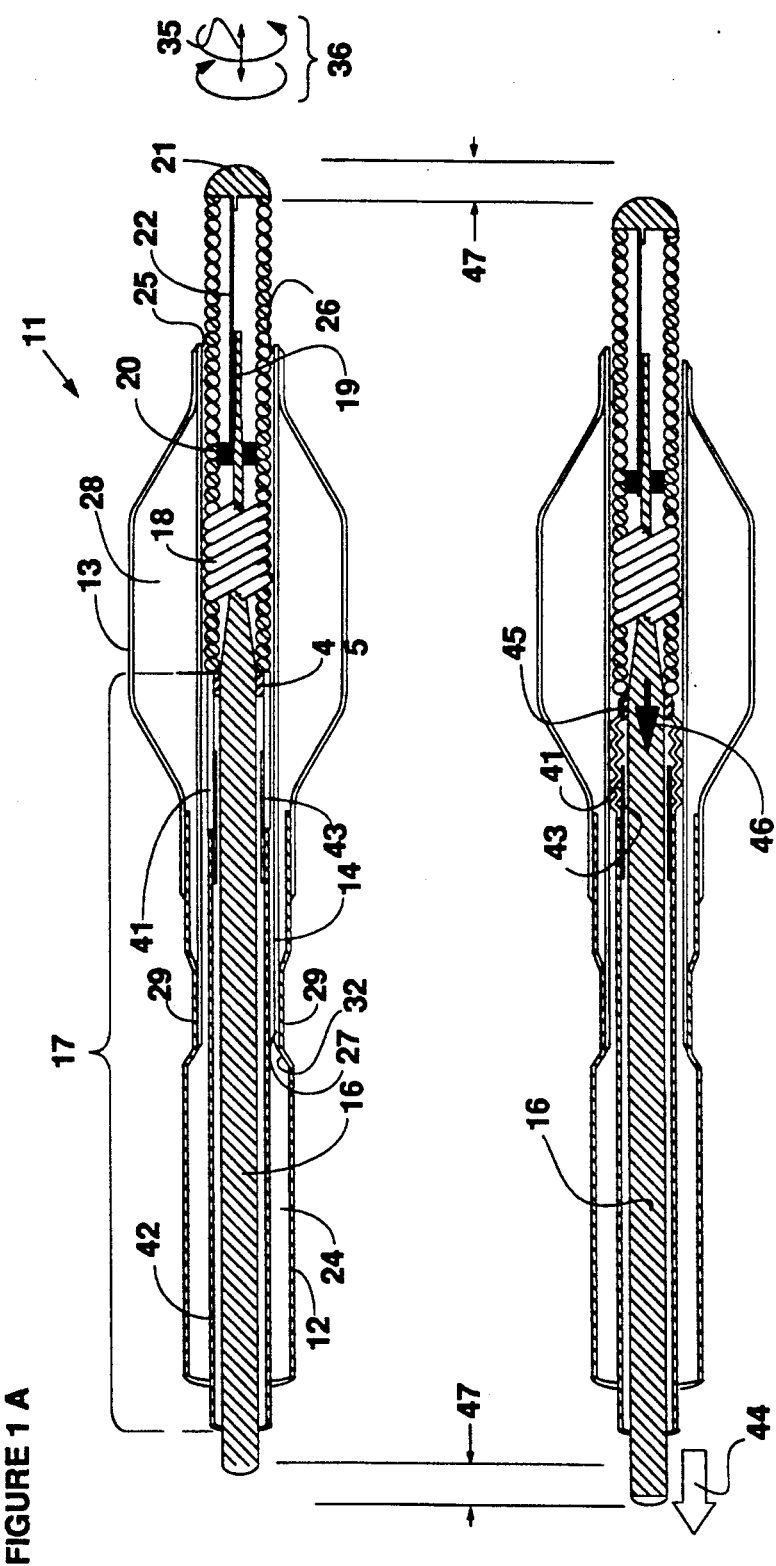

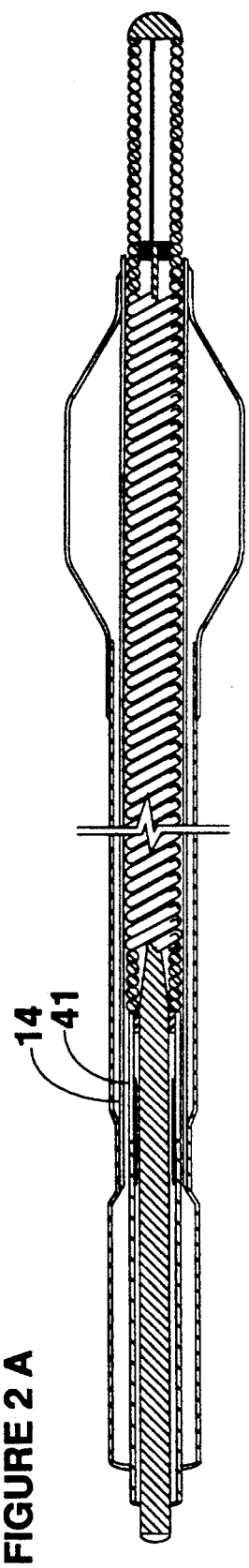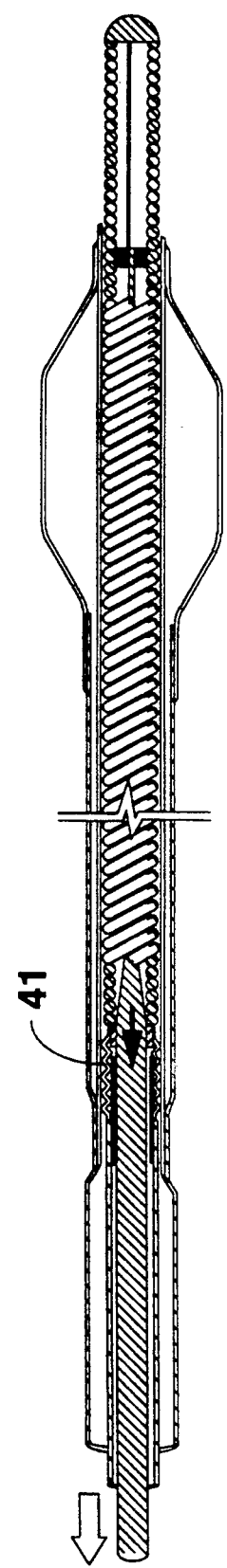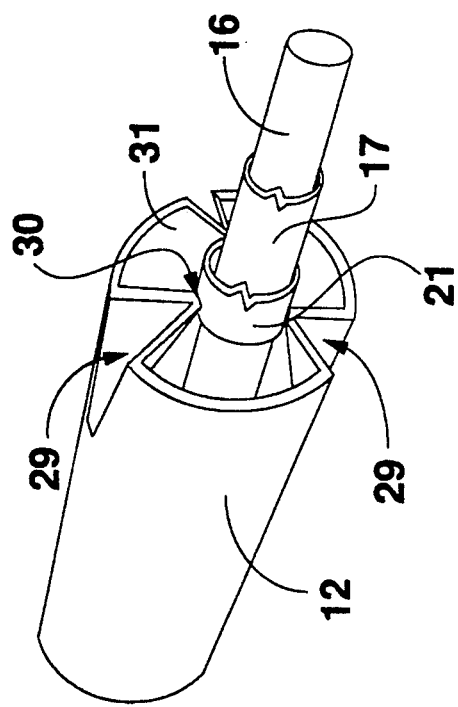

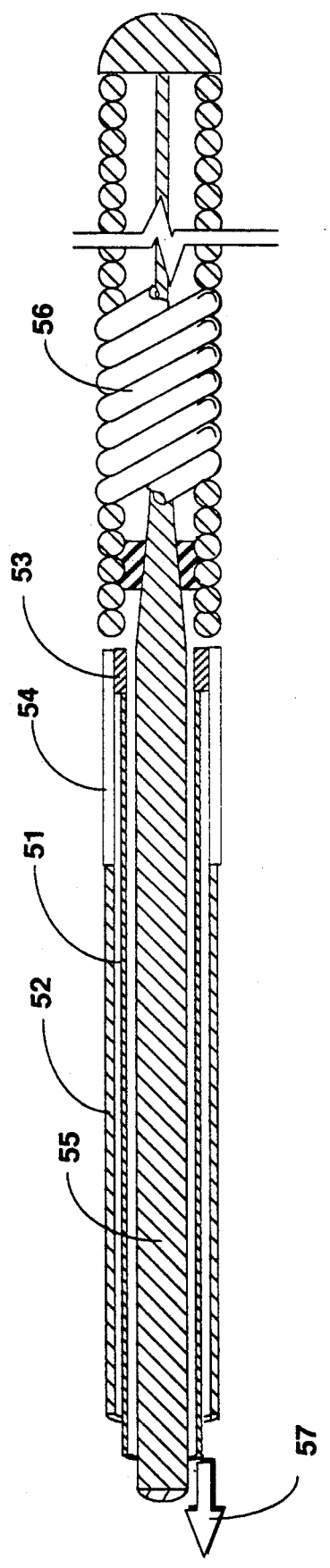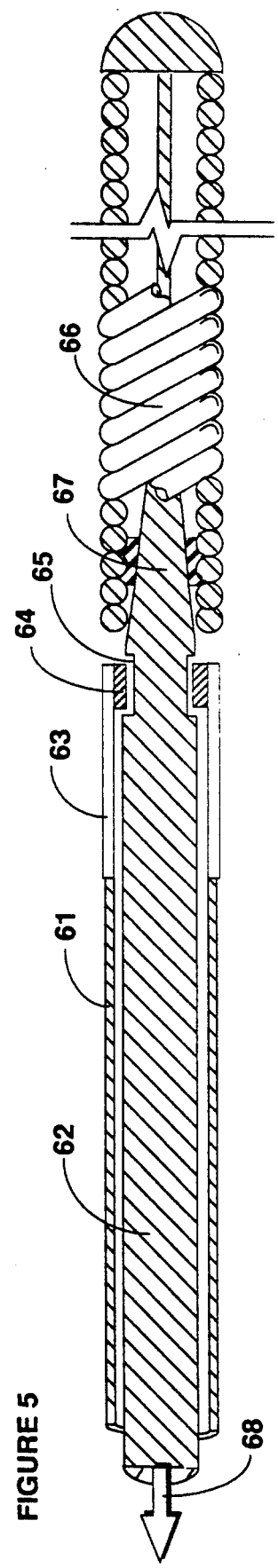
FIGURE 4
FIGURE 5

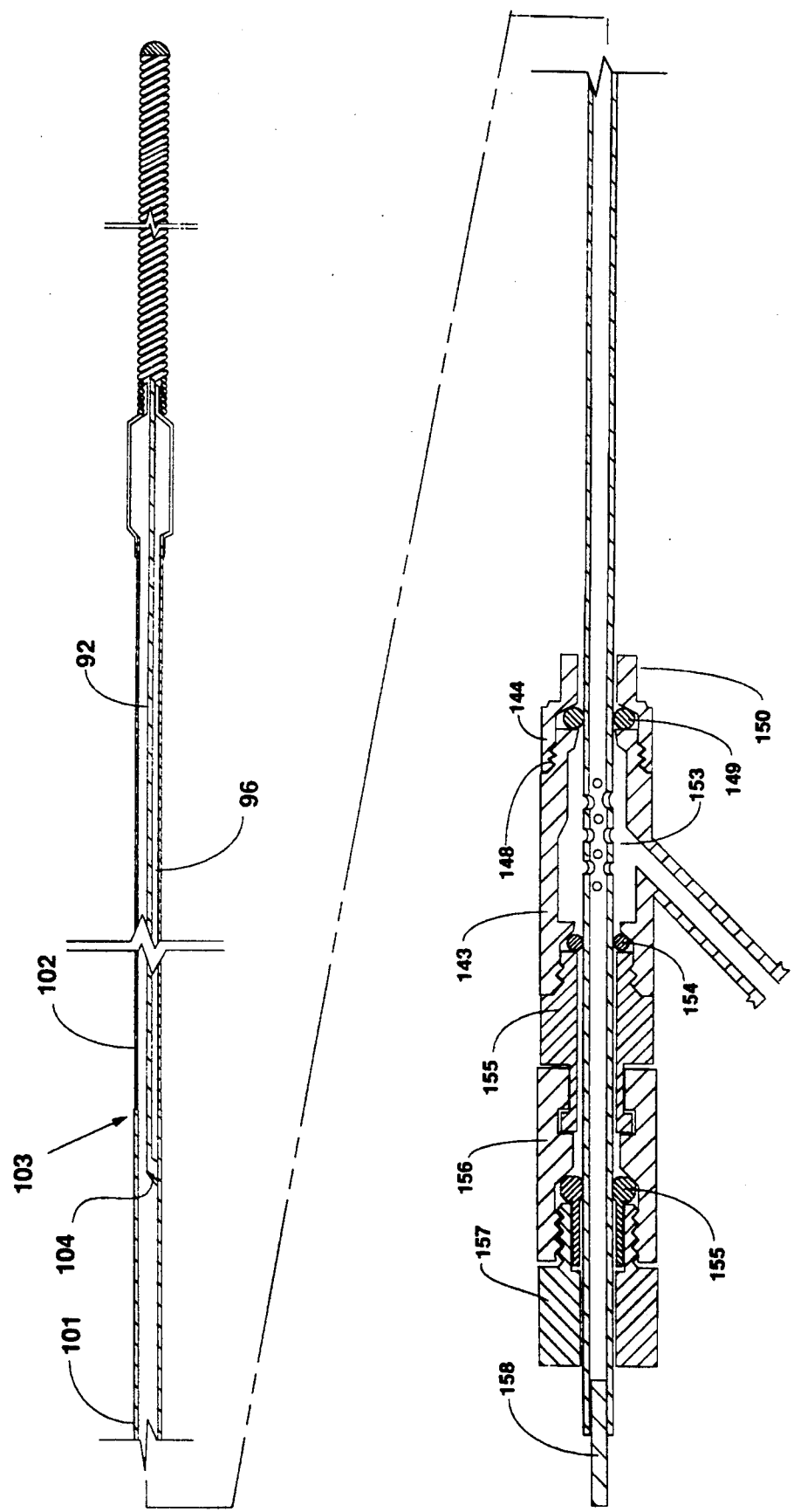

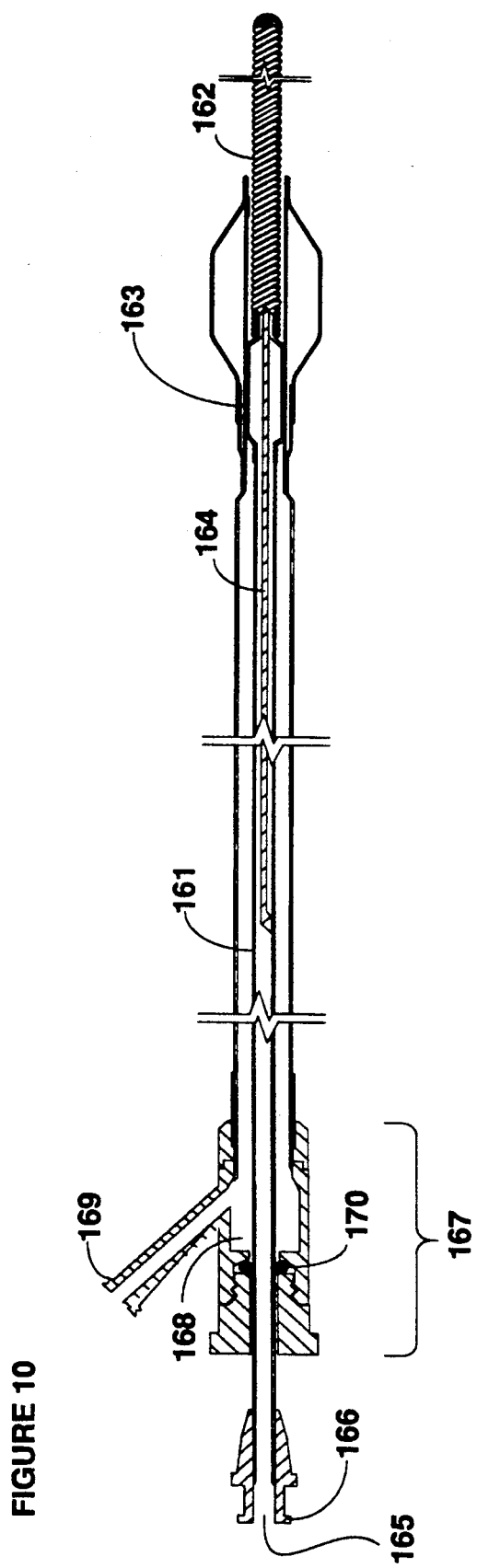

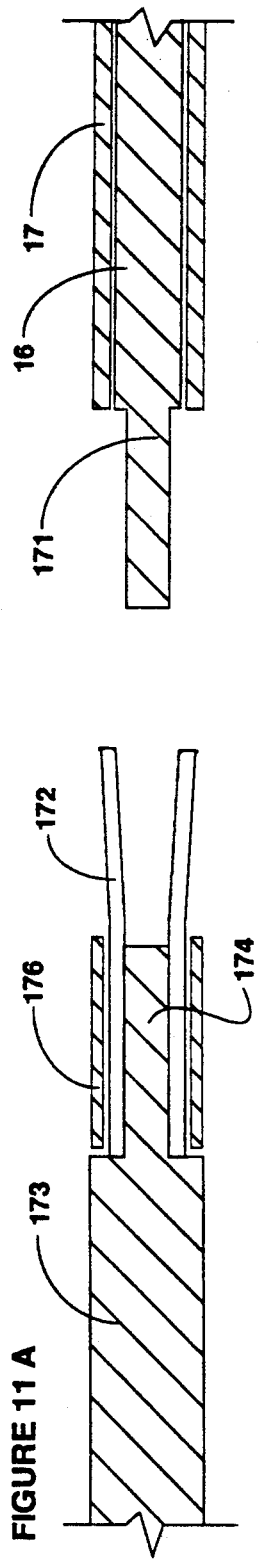
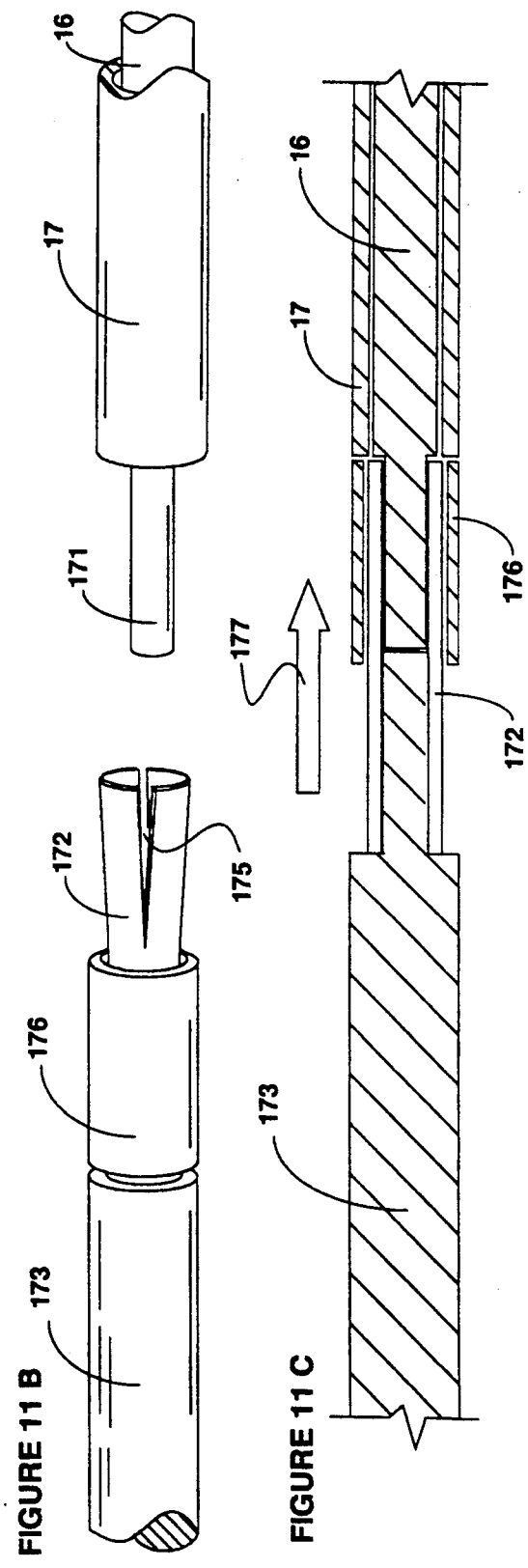
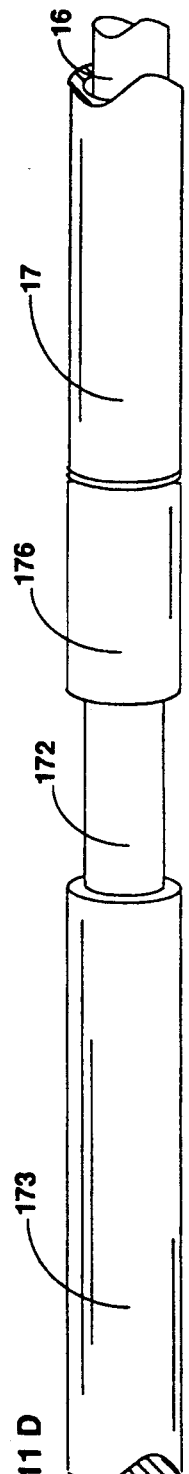
FIGURE 11 A
FIGURE 11 B
FIGURE 11 C
FIGURE 11 D

GUIDEWIRE WITH REVERSIBLE CONTACT SEAL FOR RELEASABLE SECUREMENT TO CATHETER

This invention relates to guidewires, catheters and to catheter-guidewire systems, and in particular to "exchangeable" guidewires, catheters and catheter-guidewire systems.

BACKGROUND OF THE INVENTION

Catheter-guidewire systems of many different types are used in a wide variety of medical procedures. Some of the many types of catheter-guidewire systems are angioscopic catheter systems, angioplasty catheter systems, genito-urinary catheter systems, laser catheter systems and delivery catheter systems; some are intended for diagnostic purposes, and some for therapeutic purposes including balloon dilatation and the delivery of appliances, drugs, contrast media or other useful fluids to internal bodily vessels.

These catheters contain features both favorable and unfavorable in terms of their utility, functionality and versatility. Many of these features can most easily be understood by examination of a single class of guidewire-directed catheter systems—i.e., dilatation balloon catheter-guidewire systems for angioplasty procedures. The following discussion will therefore focus on "exchangeable" angioplasty dilatation balloon catheter-guidewire systems, it being understood that the scope of this disclosure extends well beyond such systems to encompass all guidewire-directed catheter systems and corresponding components. For brevity, the following discussion of the prior art will focus on a comparison of the structural and performance differences between over-the-wire systems in general, and selected single-channel non-over-the-wire systems in particular, with the understanding that the features which distinguish the invention apply as well to multi-channel non-over-the-wire systems in a manner which will be readily apparent to those skilled in the art.

In recent years, angioplasty has gained widespread acceptance and use as a technique for treating atherosclerotic coronary and peripheral vascular diseases. According to this technique, a dilatation balloon catheter-guidewire system is percutaneously introduced into the patient's vasculature under fluoroscopic control until the balloon component of the system spans the confines of a vascular stenosis. Once in position, the balloon is inflated by hydraulic pressure to dilate the stenosis along its length and thereby relieve the obstruction to blood flow created by the stenosis.

The ease or difficulty of properly positioning an angioplasty dilatation balloon catheter-guidewire system inside the vasculature depends on several characteristics of the system, the most prominent being those known in the art as "steerability," "crossing profile" and "pushability."

The term "steerability" denotes the facility with which the course of the catheter-guidewire system can be controlled by the operator during advancement of the system within the confines of the vasculature. In general, the "steerability" of an angioplasty catheter-guidewire system directly depends on the rotational mobility of the guidewire component of the system within the confines of the vasculature. In the typical system, the rotational mobility of the guidewire component relative to the vasculature depends on rotational mobility of the guidewire component relative to the catheter component. Among systems which are otherwise comparable, those with superior steerability are easier to direct into regions of the vasculature requiring treatment.

The term "crossing profile" denotes the cross-sectional profile of the balloon component of the system in its deflated state. Typically, the lower the crossing profile, the less resistance the balloon will provoke and therefore the more readily the system can be advanced through stenotic lesions.

The term "pushability" denotes the degree to which the catheter and guidewire can be advanced into the vasculature without experiencing axial compression. Axial compression is the twisting, gathering or otherwise bending back of any component of the system along the system's longitudinal axis. Axial compression can occur in response to friction from the vasculature or, in the case of percutaneous transluminal coronary angioplasty, in response to friction from the guiding catheter, which is the catheter through which the angioplasty catheter-guidewire system is conducted from the vascular access site (where the system enters the patient's vasculature) to the coronary artery at the location requiring treatment. In general, the pushability of a catheter system varies directly with the axial rigidity of the structural element (typically the guidewire mandrel, catheter body or combination thereof) that provides axial support for the system. Typically, guidewire mandrels provide superior axial support relative to the catheter bodies in prior art catheter-guidewire systems. This circumstance arises because stainless steel is used in the construction of prior art mandrels whereas flexible polymers are commonly used in the construction of catheter bodies. Other things being equal, stainless steel, when rendered into a rod, typically provides superior axial support relative to flexible polymers rendered into thin-waller tubular structures. Hence, systems which rely upon the corresponding guidewire mandrel for support typically offer superior pushability relative to comparable systems which rely upon the corresponding catheter body for axial pushability. Systems that offer the optimal pushability rely upon both the catheter shaft and guidewire mandrel for axial support. Among systems which are otherwise comparable, those with superior pushability are easier to advance within the confines of severe luminal stenoses relative to systems that offer inferior pushability.

Thus, the ease of positioning a catheter system for use varies directly with the "steerability" and "pushability," and inversely with "crossing profile" of the system.

The safety of an angioplasty dilatation balloon catheter-guidewire system depends largely upon the "exchangeability," shaft profile and structural integrity of the system. The term "exchangeability" denotes the ability of the guidewire and the catheter body to be separated while inside the vasculature for purposes of removing one or the other and replacing the removed component with a substitute component which differs in some respect. The need for such an exchange arises when a component originally placed inside the vasculature is discovered subsequent to its placement to be inadequate or inappropriate for a particular stenosis. Systems having the capability of this exchange are termed "exchangeable" or "over-the-wire" systems, and they offer the advantage of allowing one component to be removed and replaced without removal of the other, the exchange thereby taking place without the need to reestablish intraluminal access. This saves time and maintains intraluminal access in the event of inadvertent vessel closure, and in so doing, lowers the risk of patient injury.

Among system which are otherwise comparable, those with lower shaft profiles are safer to use since they provoke less impairment to the surrounding flow of fluid (i.e., blood, blood subsitutes, contrast medium and medications) following installation within the vasculature and are thus less likely to provoke ischemia or to compromise the resolution of intraoperative angiography. In addition, systems with lower shaft profiles can be advanced through lower profile guide catheters and can thus be inserted into the body through smaller incisions. The lower profile thus adds to the safety of these catheters. Other features being equal, single-channel catheters can be constructed with lower shaft profiles relative to multi-channel catheters.

The ease with which a catheter system is prepared for use depends on how easily air can be removed from the system interior and how easily the guidewire component can be installed inside the catheter component. Systems in which air is vented at the distal end are easier to prepare relative to comparable systems that do not have this capability. Systems in which the guidewire is pre-installed (i.e., non-over-the-wire systems) are easier to prepare than systems in which the guidewire is installed by the user (i.e., over-the-wire systems).

Currently, there exist two fundamental types of angioplasty catheter-guidewire systems—over-the-wire systems and non-over-the-wire systems. The distinguishing characteristic which differentiates these two types is the separability, or lack thereof, of the catheter and guidewire components, and hence the exchangeability of the systems. Over-the-wire systems offer certain advantages relative to non-over-the-wire systems. These advantages include separability, which permits one to perform exchange procedures with greater safety, and steerability, which permits one to direct the course of the system within the confines of the vasculature with greater facility. Non-over-the-wire systems on the other hand, particularly single-channel non-over-the-wire systems, offer certain advantages relative to over-the-wire systems. These advantages include superior pushability, crossing profiles and shaft profiles. As a result, non-over-the-wire systems are typically easier to advance across the confines of critical stenoses and less likely to provoke intraoperative ischemia or to compromise the resolution of intraoperative angiography.

The advantages and disadvantages of selected non-over-the wire systems vis-à-vis over-the-wire systems relate, in part, to the practice of bonding the catheter component (and, in particular, the distal balloon component) to the guidewire in the construction of these systems. Samson, W. J., U.S. Pat. No. 4,582,181, Apr. 15, 1986, and Crittenden, J. F., U.S. Pat. No. 4,917,088, Apr. 17, 1990, describe distinct single-channel non-over-the-wire systems that contain such bonds at the distal catheter-guidewire interface. In these and similar systems, the bond between the balloon and guidewire serves several functions:

(1) It joins the distal aspect of the balloon to the guidewire;

(2) It prevents fluid and gas leakage from the distal aspect of the hydraulic channel and balloon, with the result that systems can be constructed with single channels and thus lower shaft profiles; and (3) It permits the guidewire to support the balloon against the possibility of axial collapse as the balloon is being advanced through a stenosis, and at the same time confers the axial support of the guidewire to the catheter component, thereby enhancing the pushability of the system as a whole.

In short, this bond permits one to construct non-over-the-wire systems with lower shaft profiles and superior pushability relative to over-the-wire systems, which do not contain such bonds and which rely upon the respective catheter bodies for column support. For these and other reasons, this bond is fundamental to the structure and function of most single-channel non-over-the-wire (i.e., fixed-wire and balloon-on-a-wire) devices.

The advantages of the bond are offset, however, by its permanent nature. The permanence of the bond is detrimental in a variety of ways to the structure and function of systems containing such a bond.

First, systems containing such a bond are non-exchangeable which limits the safety of these systems.

Second, the permanence of the bond compromises the steerability of the system. The bond tethers the catheter tube to the guidewire. The catheter tube is substantially larger than the guidewire in cross-sectional profile, and as a result, is more resistant to rotation within a body vessel. By tethering the guidewire to the catheter tube, the bond transmits the rotational resistance of both the catheter tube and the balloon to the guidewire. This in turn limits the ease with which the guidewire can be rotated within a body vessel, thereby compromising the steerability of the entire system.

Third, the permanence of the bond compromises the structural integrity of the system. Torsional stress develops within the catheter and guidewire components in the region of the bond when the guidewire is rotated relative to the catheter tube. If this stress is great enough, it can produce tears within the balloon component and fractures within the guidewire component of the system. The bond eliminates any possibility of relief of this stress upon continued rotation of the guidewire in one direction.

In summary, the bond between the balloon and the guidewire confers advantages in terms of shaft profile and pushability, and disadvantages in terms of exchangeability, steerability and structural integrity. The advantages stem from (1) the fact that the system can be constructed with a single channel, and (2) the ability of the system to derive axial support from both the catheter and the guidewire. The disadvantages stem from the permanence of the bond.

As a result of the above considerations, the operator is currently required to choose between over-the-wire systems that offer advantages in terms of exchangeability and steerability, and non-over-the-wire systems that offer advantages in terms of pushability, shaft profile and crossing profile. From the foregoing, it can be appreciated that there exists a continuing need for catheter-guidewire systems which offer exchangeability and steerability commensurate with over-the-wire systems of the prior art, and shaft profile and pushability commensurate with certain non-over-the-wire systems of the prior art which derive column support from the guidewire rather than the catheter body. These and other needs are met by the present invention.

SUMMARY OF THE INVENTION

The present invention resides in a remotely controlled, adjustable seizing mechanism, located at a position within the confines of a catheter-guidewire system ranging from mid-length along the system to the system's distal end. The mechanism both (1) retains hydraulic fluid within the confines of the system, and (2) transmits column support from the guidewire component to the catheter component. With this mechanism, one can construct exchangeable catheter-guidewire systems which are largely single-channel and which offer shaft profile and pushability features that are superior to exchangeable systems of the prior art. Guidewire components constructed in accordance with the principles of this invention can be used in conjunction with all catheter components of exchangeable catheter-guidewire systems of the prior art. In addition, catheter components constructed in accordance with the principles of this invention can be prepared with and used with balloon-on-a-wire systems of the prior art.

In accordance with this invention, the guidewire in a guidewire-directed exchangeable catheter-guidewire system is provided with a remotely controlled, releasable seizing member. This seizing member seizes the catheter body to immobilize the catheter body in the axial direction relative to the guidewire and thereby impart the longitudinal strength of the guidewire to both the catheter body and the balloon for purposes of column support and pushability. Guidewires provided with a seizing member in accordance with this invention can be used in conjunction with all exchangeable guidewire-directed catheters, regardless of the configuration of the catheter or its use. For such catheters, and in particular for dilatation balloon catheters which require the transmission of hydraulic pressure along their length, the seizing member can be adjusted (1) to vent air from the distal confines of the system, (2) to permit delivery of fluid from the confines of the system into a body vessel distal to the system, or (3) to retain fluid under pressure within the confines of the system and thereby facilitate hydraulic inflation of the balloon component. The result is a variety of novel, largely single-channel, fully exchangeable and optionally fluid-tight catheter-guidewire systems which have lower shaft profiles and superior pushability relative to exchangeable catheter-guidewire systems of the prior art, which are typically multi-channel systems.

By implementation of the seizing member in catheter design and procedures involving catheter use, the invention has a variety of aspects. In one aspect, the invention lies in a guidewire assembly which has an outer surface containing a section located anywhere from the mid-region of the guidewire to its distal end, which can be expanded by manipulations at or near the proximal end. This guidewire assembly is useful with any type of over-the-wire catheter body. For example, this assembly can be used to enhance the pushability of any over-the-wire catheter without compromising the exchangeability and hence safety of the system. The mechanism and structure of the seizing member permits the guidewire assembly to seize the catheter body at any position along the length of the catheter. In certain embodiments of the invention the seizing member is an hydraulically expandable element, and these embodiments further offer the option of performing sequential balloon dilatation, the details of which are given in subsequent portions of this specification. The proximal end of the guidewire assembly is adapted for the attachment of a guidewire extension so that the catheter body can be removed from the guidewire assembly and substituted with another catheter body without sacrificing intravascular access, i.e., without the need to remove the guidewire assembly once it has been advanced into position inside a vasculature. The mechanism and structure of the seizing member permits the guidewire assembly to seize the catheter body at any position along the length of the catheter.

In another aspect, the invention lies in a composite balloon catheter/guidewire system in which the balloon catheter is a single-lumen catheter for a major portion, preferably at least most, of its length. This aspect offers several advantages, including superior shaft profile and pushability with adjustable steerability, while providing steerability, exchangeability and structural integrity comparable to over-the-wire (typically multi-channel) dilatation balloon catheter-guidewire systems of the prior art. The seizing member in this aspect of the invention can also be adjusted to selectively permit the venting of air while retaining liquid, which is useful when preparing the system for use with contrast media. In those embodiments in which the seizing member is an hydraulically expandable element, this aspect of the invention further offers the option of sequential balloon dilatation. Use of the hydraulically expandable element permits the system to have two balloons of differing size. The two balloons can be used sequentially by advancing one balloon relative to the other, and the smaller balloon can serve additional functions. As in other aspects of the invention, the proximal end of the guidewire assembly is adapted for the attachment of a guidewire extension. This permits the catheter body to be removed from the guidewire assembly and substituted with another catheter body without sacrificing intravascular access, i.e., without the need to remove the guidewire assembly from the vasculature once it has been advanced into position. Guidewire assemblies containing this hydraulically expandable element can also be advanced into a vasculature and used to dilate a stenosis independently of the corresponding catheter component. Use of the guidewire assembly alone in this manner provides a very low profile device for intravasculature dilatation, a device which can then be extended by a guidewire extension to permit the introduction of a catheter component for further dilatation, without the need to sacrifice intraluminal access.

In a third aspect, the invention resides in the use of a conventional balloon-on-a-wire catheter in combination with an over-the-wire catheter body, with the balloon-on-a-wire catheter inside and serving as the guidewire for the over-the-wire catheter body. The balloon-on-a-wire catheter in this combination can be used to serve its normal function with its balloon dilating a lesion. With the balloon retracted inside the outer catheter body, however, the balloon may be used as a seizing member to impart guidewire-mediated pushability to the outer catheter body, and as a seal against loss of hydraulic fluid from the outer catheter body. Similar to the system described in the preceding paragraph, this combination may thus contain two balloons of differing size. The over-the-wire catheter body may be an exchangeable balloon dilatation catheter which is single-channel for most of its length. The shaft profile of such a system is lower than that of the system one would obtain by combining a conventional multi-channel catheter with a conventional balloon-on-a-wire device.

Conventional balloon-on-a-wire devices cannot be extended, however. To perform an exchange procedure with a combination system of this type, one must first replace the balloon-on-a-wire device with a guidewire which is either extendable or itself of extended length.

In each of these aspects and embodiments of the invention, engagement of the seizing member with, as well as its release from, the catheter body is achieved from the proximal end of the guidewire, without removal of the system from the vasculature or other bodily vessel in which it has been inserted. For balloon dilatation catheters, this may be accomplished while the balloon is in position across or in the vicinity of a stenosis.

The guidewire is part of a guidewire assembly and the seizing member consists of a deformable section on the outer surface of the guidewire assembly. The deformable section is capable of being deformed in various ways, depending on its structure. In each case, however, the deformation causes the section to expand and fill the annular space between it and the catheter body assembly, thereby seizing the guidewire assembly to the catheter body. For balloon catheters, the deformable section will be positioned at an appropriate location in the catheter body assembly such that communication between the balloon and the catheter lumen is maintained.

The site within the catheter body assembly at which the seizing member seizes the catheter may vary. For balloon catheters, the site may be located distal to the balloon, proximal to the balloon, or within the confines of the balloon. When used in conjunction with exchangeable balloon catheters of conventional design that contain distinct guidewire and hydraulic channels extending throughout their length, the seizing member can engage the catheter body at any position along the entire length of the catheter body. In certain preferred embodiments of this invention, however, the invention is applied to catheter constructions which contain a single-channel section at the proximal end and a multi-channel section at the distal end. With these catheters, the sites at which the seizing member engages the catheter body may also vary but are limited to the length of the multi-channel section. When seizing the catheter at a site in this section, the seizing member forms a seal which permits inflation and deflation of the balloon without leakage of the contents of the balloon into the vasculature.

In certain further preferred embodiments of this invention, the invention is applied to catheter constructions for which the catheter body assembly includes an internal tube of sufficient strength to provide column support to the balloon and possibly the catheter body as well. This column support tube extends at least the full length of the balloon, the distal end of the tube being securely joined to the opening at the distal end of the balloon, and the proximal end of the tube being securely joined to the catheter body either at the proximal end of the balloon or at some location removed from the balloon in the proximal direction, while still permitting fluid communication between the catheter lumen and the balloon. In this type of catheter construction, the guidewire assembly can pass through this column support tube, and the seizing member engages the catheter body assembly by seizing the inner surface of this column support tube.

For embodiments in which optimal pushability is desired, the site of engagement is at a location as far distal along the catheter assembly as possible. This allows for the optimal transmission of longitudinal strength from the guidewire to the outer catheter tube. For embodiments in which optimal flexibility at the distal end of the system and hence trackability are desired, the site of engagement will optimally be located a distance, generally 2–40 cm, proximal to the balloon. This will be true for those embodiments in which the system as a whole becomes more rigid in the vicinity of the site of engagement when the seizing member is expanded. This increase in rigidity can be varied by adjusting the force applied to the seizing member, and this adjustability can be used by the operator to optimize the rigidity of the system in the region surrounding the seizing member.

Two examples of deformable sections which act as the seizing member are described in detail in this specification.

In one example, the deformable section is a length of tubing of flexible, axially collapsible material which, when compressed axially, gathers into folds which bulge sufficiently to cause the section to tightly seize the inner wall of the column support tube or any other portion of the catheter body assembly which serves as the site of engagement. The collapsible tubing may have a bellows configuration to facilitate the formation of the folds, or it may merely be soft flexible material.

The formation of the folds to engage the catheter, and the extension of the section to eliminate the folds and thereby release the catheter, are achieved by various means. One such means is by constructing the guidewire assembly to include a hollow tube with a rod passing through its center. The collapsible tubing is a segment of the hollow tube, and the rod and hollow tube are joined at the distal end of the axially collapsible section. Axial collapse and reextension of the collapsible tubing section are then achieved by moving the rod back and forth relative to the hollow tube.

In many guidewire designs, the tip of the guidewire emerging from the distal end of the catheter body is specially constructed to permit directional control of the composite system. If, in the structure discussed in the preceding paragraph, the tip is affixed to either the hollow tube or the central rod, the tip will move longitudinally relative to the catheter body as the collapsible section is collapsed. This may be avoided by incorporating an intermediate hollow tube between the hollow tube bearing the collapsible section and the central rod, and affixing the guidewire tip to the central rod. The intermediate tube will then be joined to the outer tube at a location distal to the collapsible section, and the formation of the folds will be achieved by moving the intermediate tube without disturbing either the central rod or the catheter body.

The second example of a deformable section described in this specification is an inflatable segment of the guidewire assembly which expands upon inflation to seize the catheter body assembly at the site of engagement. This segment may for example be a length of elastic inflatable tubing formed from a relatively compliant material. Alternatively, this inflatable segment can be a prefomrmed balloon formed from relatively compliant or non-compliant materials. For clarity, this inflatable segment of the guidewire assembly will be referred to in this specification as the "secondary balloon" to distinguish it from the balloon on the catheter assembly, which will be referred to as the "primary balloon." Deformation (i.e., inflation) of the secondary balloon will be achieved by pressurizing its interior in a manner similar to but independent of the inflation of the primary balloon. The secondary balloon accordingly will have no means of fluid communication with the primary balloon or the inflation lumen which surrounds the secondary balloon and leads to the primary balloon. A central rod may be included for added pushability, but will not be involved in the engagement or disengagement of the guidewire and the catheter body.

In each of these embodiments and others within the scope of the invention, the catheter body may be constructed essentially with a single lumen, multiple lumens, or a combination thereof (varying along the length of the system). However, seizing member that retain fluid under pressure eliminate the need to separate the hydraulic and guidewire channels along the entire length of the catheter component in order to achieve a catheter-guidewire system which is both hydraulically competent and exchangeable. By allowing the passage of both the guidewire and the hydraulic fluid through the same lumen and incorporating the adjustable seizing and sealing qualities of the invention into the guidewire construction, one may construct a catheter-guidewire system with the pushability and shaft cross-sectional profile attributes of essentially single-channel non-over-the-wire catheter systems and yet preserve the exchangeability, steerability and structural integrity of over-the-wire catheter systems. This represents a major advance in the utility and versatility of catheter systems. The term "essentially single-channel" as used herein refers to a catheter system which is single channel over most if not all of its length, and particularly those whose shafts are single-channel for the full length of the shaft except for a short segment of no more than about 3 cm in length at the distal end of the shaft.

Certain embodiments of the seizing member of the invention permit the guidewire component to be rotated relative to the catheter component in an unrestricted manner when the seizing member is in the deformed (and hence seized) condition. Others do not permit such unrestricted mobility. Catheter systems which lack this mobility, however, can be adjusted by the operator to disengage the seizing member and thereby release the guidewire from the catheter and balloon. The system is thus provided with the characteristic steerability of over-the-wire systems. Although the release of the seizing member compromises the pushability and hydraulic competence of these systems, it should be recognized that, in dilatation balloon catheters in which the balloon is used to treat a lesion by dilatation, steerability is most needed when advancing the balloon toward the region of the lesion requiring treatment, that pushability is most needed when advancing the balloon across the confines of the lesion, and that hydraulic competence is most needed after the balloon is in place and ready for dilatation. Releasing the catheter and guidewire components enables the operator to more easily advance the system toward the region of the lesion requiring treatment. Seizing the catheter and guidewire components enables the operator to more easily advance the balloon across the lesion and thereafter inflate the balloon without loss of hydraulic pressure. Steerability, pushability and hydraulic competence are thus critical during different phases of an angioplasty procedure. Systems embodying this invention thus enable the operator to optimize the performance of the device at each phase to meet the needs of that phase.

The invention has applicability to percutaneous guidewire-directed catheter systems in general, including catheters for diagnostic uses as well as catheters for therapeutic uses such as drug delivery or balloon dilatation. Examples of balloon dilatation systems are transluminal coronary balloon dilatation catheters, transluminal peripheral balloon dilatation catheters, valvuloplasty catheters, intracranial intravascular catheters, and genito-urinary dilatation catheters. While the description in this specification focuses on guidewire-directed angioplasty dilatation balloon catheter systems, this is done with the understanding that analogous description applies to other catheter systems.

To summarize the application of the invention as it might be applied to dilatation balloon catheters in the treatment of a stenosis in a vasculature, the ease with which the guidewire assembly is secured to and released from the catheter body permits one to:

(a) use the guidewire assembly to enhance column support of the catheter body during the initial placement of the combination inside the vasulature and across a stenosis;

(b) obtain a pressure-tolerant hydraulic seal for the balloon during use of the balloon in the dilatation of a stenosis;

(c) open the seal to permit the evacuation of air from the distal confines of the catheter during preparation of the catheter with hydraulic fluid (contrast medium) and then close the seal to retain the hydraulic fluid under pressure, thereby circumventing the need to pull a vacuum on the system to remove the air contained within the system during preparation of the device;

(d) open the seal to perfuse a fluid out through the tip of the catheter into the vasculature, and then reclose the seal after the perfusion has been completed, both without removing either the guidewire or the catheter body from the vasculature;

(e) rotate the guidewire relative to the catheter body for purposes of steerability without subjecting either the guidewire or the catheter body to torsional shear; and (f) disengage the guidewire assembly from the catheter body for purposes of removing either one alone, and re-establish the engagement once a substitute component has been installed.

Further features, objects and advantages of the invention will be apparent from the description which follows.

BRIEF DESCRIPTION OF THE DRAWINGS

FIGS. 1A and 1B are side cross-section views of the distal end of a dilatation balloon catheter-guidewire system illustrating one embodiment of the invention. The catheter and guidewire are shown in the disengaged configuration in FIG. 1A, and in the engaged configuration in FIG. 1B.

FIGS. 2A and 2B depict a second embodiment of the invention, in the same views as those of FIGS. 1A and 1B. This embodiment differs from that of FIGS. 1A and 1B in the location of the seizing member, which has been moved in the proximal direction, i.e., to the left.

FIG. 3 is a perspective view in cutaway of the support structure for the column support tube included in each of the catheter-guidewire systems of FIGS. 1A and 1B and FIGS. 2A and 2B.

FIG. 4 is a side cross-section view of the distal end of a third embodiment of a guidewire assembly in accordance with the invention.

FIG. 5 is a side cross-section view of the distal end of a fourth embodiment of a guidewire assembly in accordance with the invention.

FIG. 9A shows the proximal end only, while FIG. 9B is a full-length view of a portion of the structure of FIG. 9A.

FIG. 10 illustrates a seventh embodiment of the invention, in a cross-section view showing both distal and proximal ends. This embodiment is the combination of a conventional balloon-on-a-wire device and a largely single-channel over-the-wire catheter, in which the balloon-on-a-wire device serves as the guidewire assembly.

FIGS. 11A through 11D illustrate a guidewire extension mechanism suitable for use in conjunction with the systems depicted in the preceding figures. FIGS. 11A and 11B show the guidewire and guidewire extension with the coupling joint disengaged, in side cross-section and perspective views, respectively. FIGS. 11C and 11D are similar views showing the guidewire and guidewire extension with the coupling joint engaged.

DETAILED DESCRIPTION OF THE INVENTION AND PREFERRED EMBODIMENTS

Figure 6:
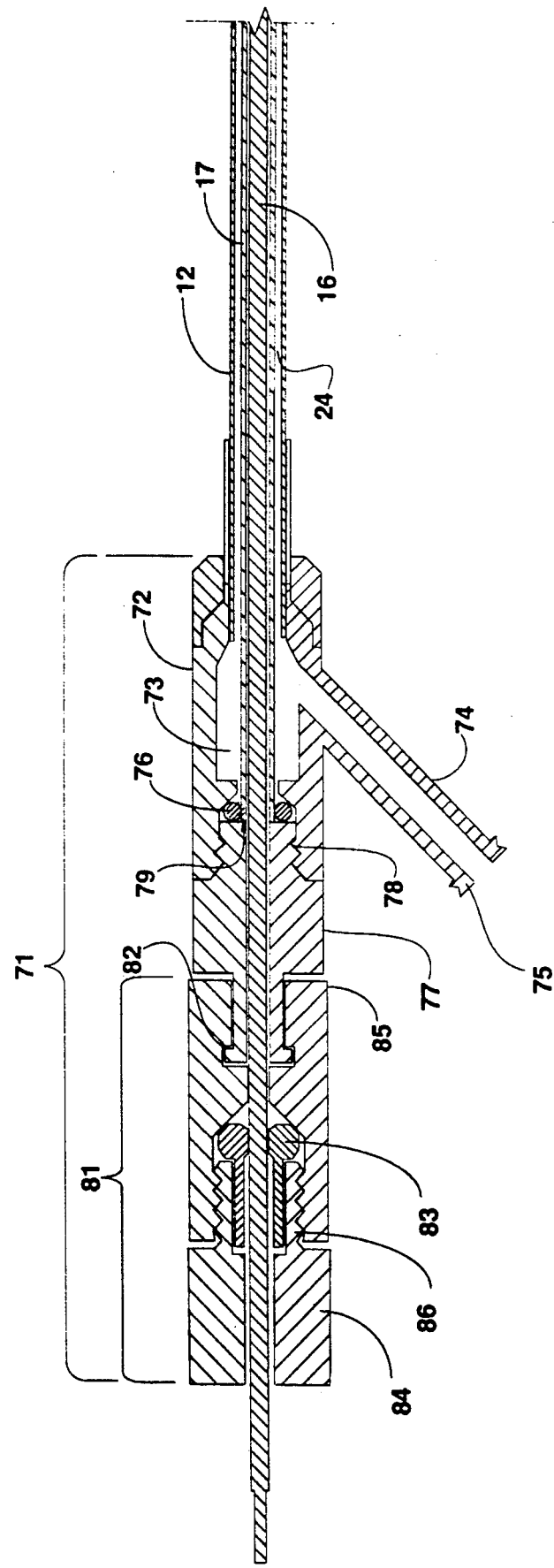
FIG. 6 is a side cross-section view of the proximal end of each of the systems shown in the previous figures.

While this invention is of broad scope and capable of use in a wide range of catheter constructions, the basic elements of the invention and their functions are most easily understood by examination of dilation balloon catheter systems, and in particular, a few specific embodiments.

FIGS. 1A and 1B depict the distal end of a dilatation balloon catheter system 11. The system includes a catheter body assembly and a guidewire assembly. The components of the catheter body assembly which are visible in the drawing are a cylindrical outer catheter tube 12, a cylindrical balloon 13 which is inflated for dilatation of a stenosis, and a cylindrical column support tube 14 inside the balloon. The components of the guidewire assembly which are visible in the drawing are a solid cylindrical rod 16 (which may alternatively be a hollow tube), a cylindrical tube 17 encircling the rod 16, and a flexible tip 18 at the distal end of the assembly. The flexible tip 18 is a coil of wire which surrounds the tapered end 19 of the rod 16 and is secured to the rod by a solder joint 20. The flexible tip 18 terminates at its own distal end in a rounded knob 21, and contains an internal shaping ribbon 22 which imparts a curvature to the tip (in a plane perpendicular to the plane of the figure).

The catheter body assembly contains a single lumen 24 for passage of both the guidewire assembly and fluids for either inflation of the balloon 13 or perfusion outward through the opening 25 at the distal end of the catheter body assembly. The guidewire assembly passes through the column support tube 14 and out the distal opening 25. This permits the curved tip 18 of the guidewire assembly to extend distally from the catheter body to allow its use in guiding and steering the combined components through the vasculature. The distal end 26 of the column support tube is bonded to the distal end of the balloon 13 around the full circumference of the column support tube 14 in a pressure-tolerant and hydraulically competent seal. The proximal end 27 of the column support tube is supported by and bonded to the outer catheter tube 12 at a location on the proximal side of the balloon.

The junction between the proximal end of the column support tube and the outer catheter tube is one which permits fluid communication between the catheter lumen 24 and the balloon interior 28. To achieve this, the junction is formed by indentations 29 in the outer catheter tube 12, spaced periodically about its circumference. These indentations are shown in sectional perspective in FIG. 3. The inner crests 30 of the indentations are in contact with and bonded to the outer surface of the column support tube 14. Fluid communication occurs through the channels 31 between the indentations. The proximal ends 32 of the indentations slope inward toward the column support tube 14 in a tapering manner to guide the insertion of the guidewire assembly into the column support tube.

In the configuration shown in FIG. 1A, the guidewire assembly is free to move within the lumen 24 of the catheter body, both back and forth in the axial direction 35 and in either rotational direction 36 as well. Thus, the guidewire assembly may be entirely withdrawn from the catheter body, and likewise, the catheter body may be entirely removed from the guidewire assembly. Also, fluids in the catheter lumen 24 and the interior 28 of the balloon are free to pass through the annular clearance between the guidewire tube 17 and the column support tube 14, and out through the distal opening 25. No such mobility or fluid passage is permitted, however, when the guidewire assembly assumes the configuration shown in FIG. 1B.

The feature of the configuration of FIG. 1B which prevents axial movement of the guidewire assembly relative to the catheter body and vice-versa, and prevents fluid passage as well, is the configuration of a deformable section 41 of the cylindrical tube 17 which forms the exterior of the guidewire assembly. Unlike the remainder of the tube, i.e., the main portion 42 joined to its proximal end, the deformable section 41 is readily compressible along the system's longitudinal axis. The section has a bellows-type structure in these figures, and is shown in the compressed configuration in FIG. 1B, as opposed to the non-compressed or extended configuration in FIG. 1A. With the section in the compressed configuration, the folds of the section expand radially outward to contact the inner surface of the column support tube 14. The pressure of the contact causes the folds to seize the column support tube to the extent that the two are fused together and immobilized relative to each other, and the annular clearance between them is completely blocked, sealing the lumen 24 and balloon interior 28 to retain fluid or fluid pressure. An internal hollow post 43 bonded to the inside of the guidewire tube 17 and extending into the interior of the deformable section 41 serves to: (1) provide a platform through which the main portion 42 of the guidewire tube 17 is secured to the deformable section 41, (2) prevent inward collapse of the deformable section upon axial compression, and (3) ensure that the folds project outward uniformly to apply substantially uniform contact pressure between the two parts around the entire circumference of the guidewire.

Manipulation of the deformable section 41 is achieved by axial movement of the rod 16 relative to the tube 17. With the tube 17 held stationary, the rod 16 is pulled in the proximal direction indicated by the arrow 44. The rod and the deformable section are joined at a bond joint 45 at the distal end of the deformable section. As a result, this axial movement of the rod in the direction indicated by the arrow 46 draws the distal end of the deformable section back toward the proximal end, collapsing the deformable section 41 as shown. During this process, the rod undergoes a small axial displacement 47.

This axial movement of the rod 16 relative to the tube 17 may be achieved in any of various ways, and is not critical to the operation of the seal. It may for example be achieved by a simple manual pulling of the rod at the proximal end of the catheter system, or it may be achieved by a more controlled mechanism at the proximal end, such as a screw-type mechanism. The structure and arrangement of this and other suitable mechanisms will be readily apparent to those skilled in the art.

FIGS. 2A and 2B depict a variation on the catheter-guidewire assembly shown in FIGS. 1A and 1B. In this variation, the deformable section 41 and hence the seizing mechanism are at a location which is more proximal relative to the system as a whole than the corresponding elements of the assembly of FIGS. 1A and 1B. The column support tube 14 in this variation is correspondingly longer than its counterpart in FIGS. 1A and 1B, and the deformable section 41 is at a more proximal location on the guidewire assembly.

FIG. 4 depicts a further variation. In this variation, the guidewire tube 17 of the preceding figures is replaced by the combination of an inner tube 51 and an outer tube 52 secured together by a bond 53 at the distal end of each. The deformable (in this case, compressible) section 54 is the terminal section of the outer tube 52, and compression of the deformable section (and hence engagement of the seal) is accomplished by drawing the inner tube 51 in the proximal direction indicated by the arrow 57 while holding the outer tube 52 stationary. The solid central rod 55 in this variation is not joined to either of the two tubes, and as a result there is no axial displacement of the rod during engagement or disengagement of the seal. Accordingly, since the flexible tip 56 of the guidewire assembly is joined only to the rod 55, engagement and disengagement of the seal does not result in any axial displacement or limitation of the rotational mobility of the flexible tip 56 of the guidewire relative to the catheter body. While the systems of FIGS. 1A, 1B, 2A and 2B provide for rotation of the rod 16 to a limited extent relative to the guidewire tube 17, the system of FIG. 4 permits infinite rotation of the rod 55 relative to the guidewire tube 52, and hence maintained steerability regardless of whether or not the deformable section 54 is seizing the catheter body.

The guidewire assembly depicted in FIG. 4 may be substituted for the guidewire tube 17 and rod 16 assembly of FIGS. 1A, 1B, 2A and 2B, and thus used with the catheter component of either of the systems illustrated in the latter figures. In either case, the result is a largely single-channel, fully exchangeable, adjustably hydraulically competent dilatation balloon catheter-guidewire system, which has superior shaft profile, adjustably superior pushability and adjustably comparable steerability relative to exchangeable systems of the prior art.

A further variation is depicted in FIG. 5. Here, as in FIGS. 1A, 1B, 2A and 2B, a single guidewire tube 61 surrounds the central rod 62, and the deformable section 63 is the terminal segment of the tube. In place of the bond joint 45 of FIGS. 1A and 1B, however, are mated surface contours in the form of an internal ring flange 64 at the distal end of the deformable section and a circumferential groove 65 on the rod 62. With the flange 64 inside the groove 65 as shown, the deformable section 63 may be axially compressed as in FIGS. 1B and 2B, by drawing the rod 62 in the proximal direction as indicated by the arrow 68 relative to the tube 61.

An advantage that the structure of FIG. 5 offers relative to that of FIGS. 1A, 1B, 2A and 2B is the lack of the need for a bond 45, and thus the elimination of the risk of the bond breaking and thereby rendering the seal entirely inoperable. The structure of FIG. 5 also permits the rod 62 to be rotated without rotating the tube 61 or the deformable section 63. Since the flexible tip 66 is secured only to the rod 62, this permits the tip to be rotated without disturbing the tube or the deformable section. Such independent rotation provides improved steerability to the structure, particularly when the deformable section is compressed and the seal between the guidewire assembly and the catheter body is thus engaged.

The arrangement of FIG. 5 may itself be varied to avoid the need to machine the circumferential groove 65 into the outer surface of the rod 62. Solid rods for use as guidewires are often tapered in stages toward the distal tip, and a groove may be formed by placing two thin cylinder sections around the rod, one behind the other with a small gap in between at a location distal to one of the tapers. The gap will then serve as the groove.

Between and subsequent to the manipulation of the various parts of the guidewire system relative to each other in each of these embodiments, the parts may be secured against further relative movement to avoid any unintentional disengagement of the guidewire from the catheter body and likewise any unintentional leakage through the seal. Securement may be achieved in a variety of ways. One structure for releasably securing the parts together in this manner is shown in FIG. 6.

The view in FIG. 6 is the proximal end of the catheter system shown in FIGS. 1A, 1B, 2A, 2B and 5, with a catheter body containing a single outer tube 12, and a guidewire assembly containing a central rod 16 and a surrounding tube 17, the deformable section (not shown) being the terminal portion of the latter. A proximal adapter 71 at the proximal end of the system serves to adjustably maintain the coaxial relationship of the longitudinal elements 12, 16, 17 of the system. This permits the operator to advance the system as a single unit within the vasculature, and it also maintains the positions of the elements of the system relative to each other, thereby maintaining the sealing mechanism in the desired condition. The proximal adapter 71 further serves as a means of rotating the elements relative to each other for purposes of steering the system through the vasculature, and, still further, it provides connections for fluid passage into and out of the catheter lumen 24 for pressurization and perfusion.

A stationary portion 72 of the proximal adapter is bonded to the outer catheter tube 12, and contains a reservoir 73 which communicates directly with the catheter lumen 24. Supply of fluid to the reservoir 73 is achieved through a side port 74 in the stationary portion. The side port 74 terminates in any conventional fitting 75, such as for example a Luer Lock fitting, suitable for the attachment of a fluid line. The guidewire tube 17 passes through the reservoir 73. An O-ring 76 surrounds the guidewire tube at the proximal end of the stationary portion, and a tightening fitting 77 which mates with the stationary portion through a threaded connection 78 compresses the O-ring against both the body of the stationary portion 72 and the guidewire tube 17. Properly adjusted, the O-ring 76 and tightening fitting 77 can prevent leakage of fluid from the reservoir 73 into the interior of the guidewire tube 17 while permitting rotational mobility of the guidewire rod 16 within the proximal confines of the catheter component of the system. The O-ring 76 can also be adjusted to seize the guidewire tube 17 and thereby fix the guidewire tube relative to the proximal adapter, thereby restraining the guidewire tube when the mandrel 16 is being advanced for the purpose of disengaging the seizing member at the distal end of the system. The tightening fitting 77 abuts the proximal end 79 of the guidewire tube and in so doing, serves a further function as an arresting element for the guidewire tube, preventing it from moving in the proximal direction as the rod 16 is drawn backward the short distance required to actuate the seal.

The portion of the proximal adapter 71 which provides control of the guidewire rod 16 is a rotator 81 joined to the tightening fitting 77 by a freely rotatable connection 82. The rotator is constructed in three elements—a pin-vise 83 (a cylindrical gripping member with an enlarged rim and narrowed opening at its distal end) surrounding the guidewire rod 16, and male 84 and female 85 members engaged through a screw connection 86. Tightening of the male and female members together closes and compresses the pin-vise 83 around the guidewire rod 16, clamping the rod against either rotational or axial movement. With the rod thus clamped, the rod may be rotated by rotating the rotator 81. To move the rod for purposes of manipulating the seal at the distal portion of the system, the grip of the pin-vise 83 is loosened by turning the male member 84 in the opposite direction relative to the female member 85. Once the rod is in the desired position, the pin-vise is clamped down again to hold the position. The pin-vise may be tightened with the rod at any position relative to the remainder of the system, and the pin-vise may be adjusted to any degree of tightness.

In addition to the functions described above, the proximal adapter 71 can be manipulated to free the proximal ends of the catheter and guidewire from each other. Once this is done, the catheter body can be removed from the guidewire assembly while leaving the guidewire assembly inside the vasculature. Likewise, the guidewire assembly can be removed from the catheter body while leaving the catheter body inside the vasculature. Prior to performing either of these manipulations, the seizing mechanism at the distal end of the system must also be disengaged, as well as secured to prevent it from inadvertently re-engaging. As indicated above, engagement, disengagement and position maintenance for either engagement or disengagement are all achieved by remote control through manipulations of the proximal adapter. These manipulations involve (1) the O-ring 76, part of whose function is to hold back the guidewire tube 17 while the mandrel 16 is being advanced to disengage the seizing member at the distal end of the system, (2) the tightening fitting 77 in its function as an arresting element to hold the guidewire tube stationary as the mandrel 16 is drawn backward, and (3) the pin-vise 83 to releasably secure the guidewire mandrel 16 to the proximal adapter.

To remove the catheter body, one first affixes an extension wire to the guidewire at its proximal end in accordance with methods known in the art, to approximately double the length of the guidewire. Examples of guidewire extensions and methods by which they are attached to the guidewire are illustrated in FIGS. 11A, 11B, 11C and 11D, and are discussed in detail below. The attachment of the extension permits the catheter body to be withdrawn entirely from the vasculature without losing access to the guidewire assembly. Once the extension is attached, the male and female portions of the rotator 81 are loosened to relax the pin-vise 83 surrounding the guidewire rod, thereby releasing the guidewire rod 16 and permitting it to be advanced relative to the guidewire tubing 17 while the guidewire tubing is held in a fixed axial position relative to the catheter tube 12 by the O-ring 76. The guidewire rod 16 is then advanced relative to the guidewire tubing 17 to relax (i.e., longitudinally extend) the deformable section at the distal end of the guidewire assembly and thereby uncouple the seizure between the guidewire assembly and the catheter body. Once the seizure is relieved in this manner, the tightening fitting 77 is loosened to relax the O-ring 76 surrounding the proximal end of the guidewire tube 17, thereby releasing all components of the guidewire assembly from the catheter component of the system. The proximal adapter 71 is then drawn over the guidewire assembly and the guidewire extension as a unit, drawing with it the catheter body and leaving the guidewire assembly and the guidewire extension behind.

To remove the guidewire assembly, the male and female members of the rotator 81 are loosened so that the guidewire rod 16 can be advanced relative to the guidewire tube 17, thereby releasing the distal seizing mechanism to disengage the catheter and guidewire. The male and female members of the rotator 81 are then retightened, which causes the rotator to seize the guidewire assembly. The tightening fitting 77 is then loosened and disconnected entirely from the stationary portion 72 of the proximal adapter, thereby relieving the pressure on the O-ring 76. The rotator and the tightening fitting are then drawn away from the stationary portion, removing both the guidewire rod 16 and the guidewire tube 17 from the catheter body, the guidewire tube being attached to the rod at the distal end by either bonds or mated members as described above.

Figure 7A:
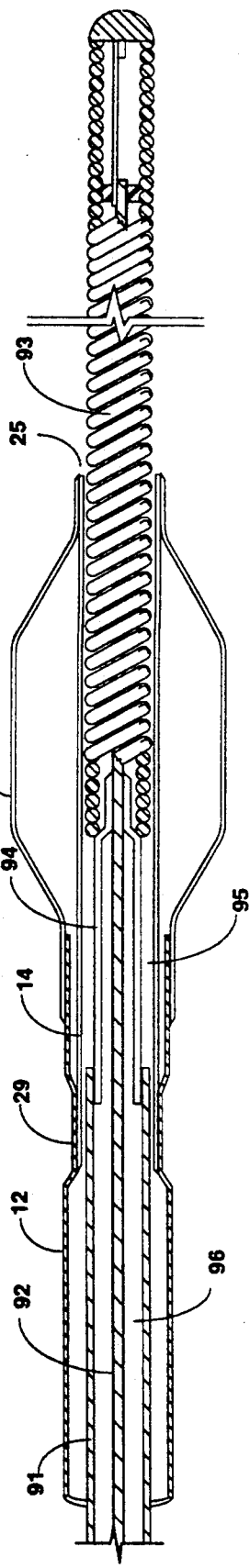
FIGS. 7A, 7B and 7C illustrate a fifth embodiment of the invention in three different configurations, again in side cross-section views of the distal end.
Figure 7B:
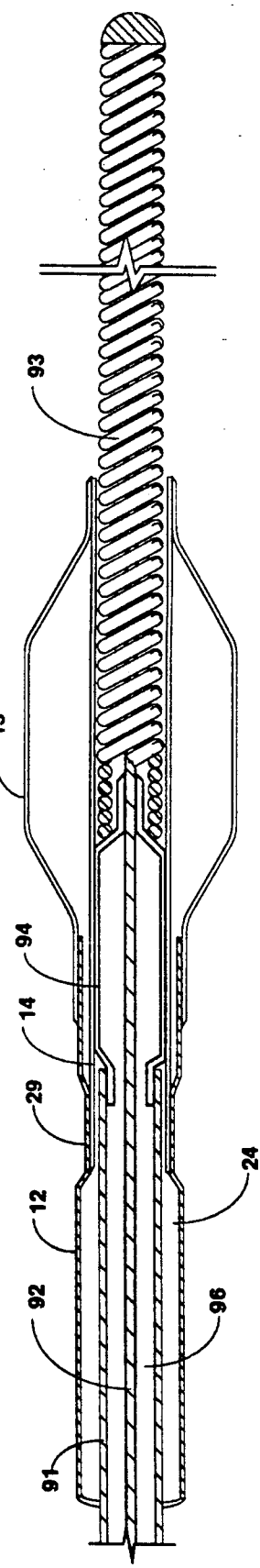
Figure 7C:
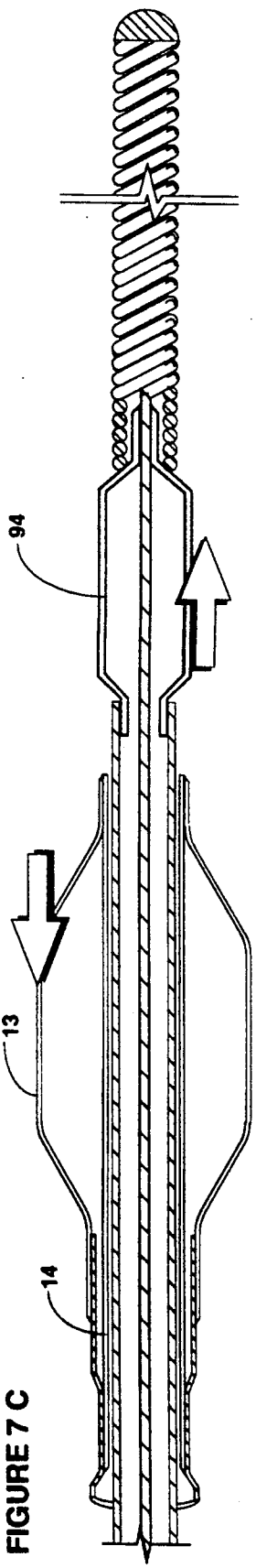

FIGS. 7A, 7B and 7C depict a catheter system with a seizing and sealing mechanism which is related to but distinct from that of the preceding figures. In this system, the catheter body assembly is the same as that of the system of FIGS. 1A and 1B, with the same outer catheter tube 12, balloon 13, and column support tube 14, the latter mounted to the outer catheter tube 12 by the same indentations 29 in the outer catheter tube. The guidewire assembly includes a number of components similar to those of FIGS. 1A, 1B, 2A and 2B, including a cylindrical tube 91, a central rod 92, and a flexible tip 93. The guidewire assembly likewise passes through the column support tube 14 and, with the seizing and sealing mechanism properly adjusted, is free to move within the catheter body assembly, both axially and rotationally, and the guidewire tip 93 emerges from the opening 25 at the distal end of the balloon. Although the catheter component of the system illustrated in FIGS. 7A, 7B and 7C resembles the corresponding component of the system illustrated in FIGS. 1A and 1B, this is but one example of a catheter component which can be used in conjunction with this seizing and sealing mechanism. A variety of catheters of different construction, such as for example the catheter component depicted in FIGS. 2A and 2B, can also be used. With the catheter component depicted in FIGS. 2A and 2B, the seizing and sealing mechanism of the system is at a location displaced a short distance in the proximal direction.

The guidewire assembly of FIGS. 7A, 7B and 7C also includes a deformable section 94, but unlike the deformable section 41 of FIGS. 1A and 1B, this section is deformed by inflation. This inflatable section is either a length of cylindrical tubing or a preformed balloon (i.e., a secondary balloon) arranged coaxially with the other components of the guidewire system, and forming the terminal portion of the guidewire tube 91. The material from which this inflatable section is made can be elastic, thereby enabling it to expand upon pressurization of its interior. Alternatively, in the case of embodiments in which the inflatable section is a preformed balloon, the inflatable section can be constructed of an inflatable and deflatable but relatively non-compliant material, and thus one which is capable of withstanding relatively high pressures. Regardless of the construction of the inflatable element, the cylindrical tube 91, to which the inflatable element is bonded is, in optimal constructions, constructed of non-compliant materials that resist expansion or rupture under pressure.

In FIG. 7A, the inflatable section is shown in a relaxed or uninflated state, leaving an annular clearance 95 between it and the column support tube 14. In FIG. 7B, the section is shown in an inflated state, eliminating the clearance and seizing the column support tube, thereby preventing both motion of the guidewire and catheter body assemblies relative to each other and leakage from the catheter lumen or balloon out to the exterior of the system. Inflation of the inflatable section is achieved by supplying pressurized inflation fluid (either liquid or gas) to the interior of the guidewire tube 96 from a source at the proximal end of the catheter system.

While the central rod 92 no longer serves as a means of actuating the seal, it is preferably still included in the guidewire assembly as it is in the embodiment shown in these drawings. Its function in this embodiment is to provide structural integrity to the guidewire assembly and to contribute to the column support of the catheter assembly. The rod also serves as a means of controlling and rotating the guidewire tip for purposes of steerability, since the tip is bonded directly to the rod by solder joints as in the embodiment of FIGS. 1A through 5.

An advantage of the use of an inflatable tubular section as the seizing and sealing element is that it does not require motion of any parts to engage and disengage the column support tube. The guidewire tip may thus be held stationary during engagement and disengagement. A second advantage is that the area of contact between the inflatable section and the column support tube is both continuous and extended over a greater distance than that achieved with the deformable section of FIGS. 1A, 1B, 2A and 2B which is deformed by axial compression. This provides both a firmer grip and greater assurance against leaks. A third advantage is that the inflatable section permits application of a greater contact pressure, further assuring both a strong seal and a strong grip.

A fourth advantage is that the inflatable section may itself be used as a dilatation balloon of a smaller inflated diameter than that of the balloon 13 on the catheter body assembly. FIG. 7C depicts the catheter system in a configuration in which this can occur. In this configuration, the guidewire assembly has been advanced far enough through the catheter body assembly that the inflatable section 94 has emerged from the opening 25 at the distal end of the balloon and is free from the confines of the column support tube 14. The inflatable section may then itself be positioned across the stenosis, and used as a preliminary means of dilatation. The pressurization for this dilatation will be supplied by the fluid used to inflate the inflatable section. Due to its narrow diameter, the inflatable section will be useful for critical stenoses which may present a high resistance to crossing by the catheter body balloon 13.

Dilatation with the guidewire inflatable section 94 may then be followed by a retraction of the guidewire assembly back in the proximal direction until the inflatable section is positioned inside the column support tube 14, i.e., the configuration shown in FIG. 7B. The inflatable section will then be inflated at least once more, this time however to seize the column support tube 14 and seal the catheter body balloon 13 and the lumen 24 communicating with it. The catheter body balloon 13 (i.e., the primary balloon) may then be advanced across the now partially dilated stenosis, and inflated by pressurization through the catheter lumen 24 to complete the dilatation of the stenosis.

Figure 8:
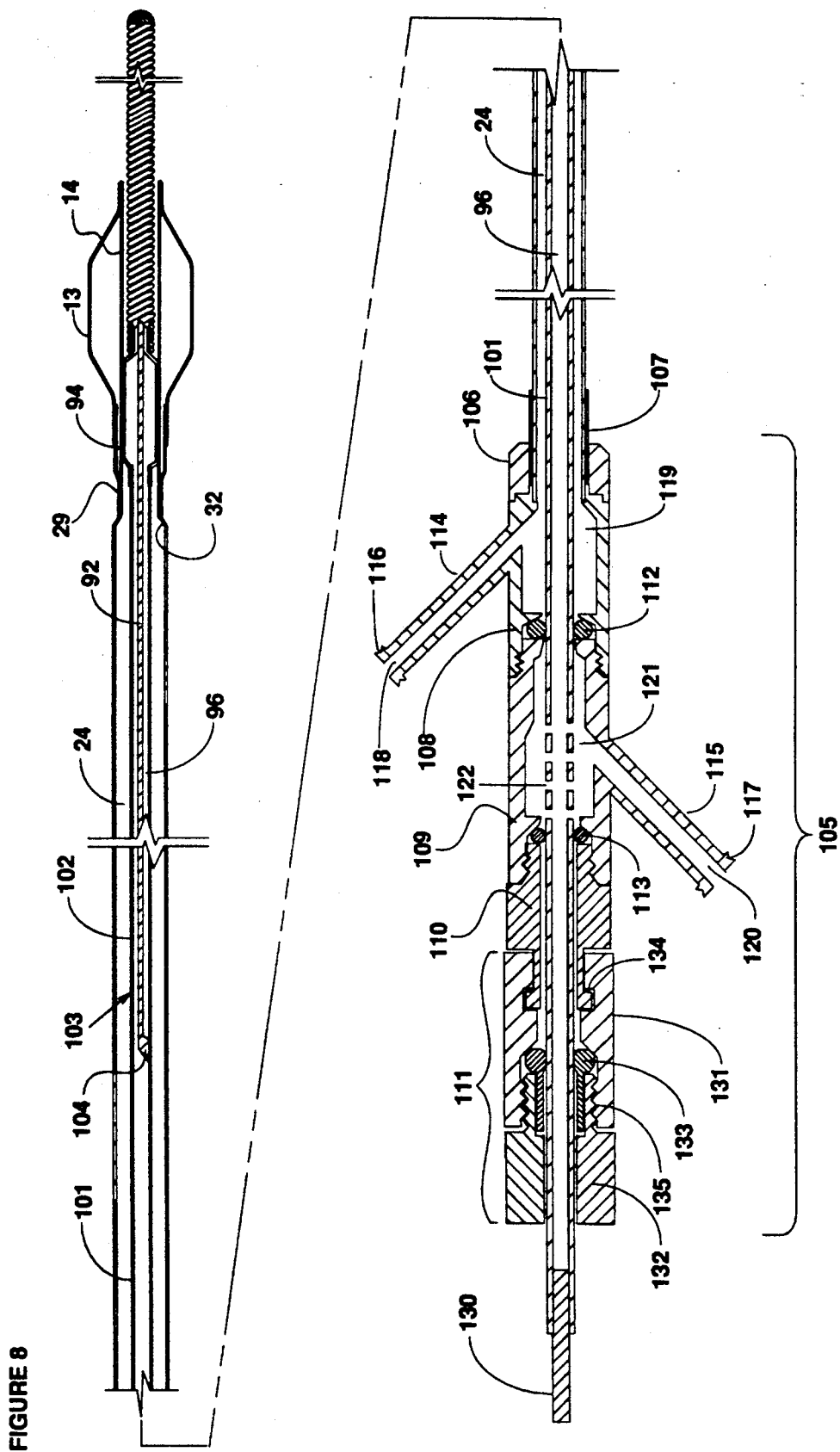
FIG. 8 illustrates the embodiment of FIGS. 7A, 7B and 7C in a full-length view, again in side cross section.

FIG. 8 is a full-length cross-section view of the catheter-guidewire system whose distal end is shown in FIGS. 7A-7C. The guidewire tube 91 of FIGS. 7A-7C is comprised of two segments—a proximal segment 101 which is relatively rigid, such as for example stainless steel, and a distal segment 102 of more flexible material. The two segments are secured together by a fluid-tight pressure-tolerant butt joint 103. The guidewire rod 92 is secured to the relatively rigid proximal segment 101 by means of a weld joint 104.

The interior 96 of the guidewire tube serves as an inner lumen through which hydraulic fluid is conveyed to the secondary balloon 94, and this lumen is surrounded by an annular lumen 24 which conveys hydraulic fluid to the primary balloon 13. The proximal adapter 105 is designed to permit the independent supply of hydraulic fluid to, and withdrawal of hydraulic fluid from, each lumen. The parts of the proximal adapter, in the order of their location extending proximally from the distal end, are a cap 106 which is mounted over a short length of tubing 107 serving as a stress riser; three typically stationary elements 108, 109, and 110 which are joined to each other by threaded screw connections, which may be either left-hand or right-hand; and a rotator 111. A first O-ring 112 is positioned at the juncture of the first and second stationary elements 108, 109, and a second O-ring 113 is positioned at the juncture of the second and third stationary elements 109, 110. A first side arm 114 extends outward at an oblique angle from the first stationary element 108, and a second side arm 115 extends outward at an oblique angle from the second stationary element 109. Each of the two side arms terminates in a rim fitting 116, 117 designed to be quickly connected and disconnected, such as a Luer Lock connection. These connections and others like them in the other drawings included here-with are typically attached to syringes containing the inflation fluids through flexible tubing terminating in a fitting which mates with the rim fittings 116, 117. The syringes are manually operated and contain a pressure gauge.

The channel 118 of the first side arm supplies a reservoir 119 in the proximal adapter which leads directly into the annular lumen 24 which supplies the primary balloon 13. The channel 120 of the second side arm supplies a second reservoir 121 which surrounds a region of the proximal end of the guidewire tube where a series of fenestrations 122, or small discrete openings in the wall of the guidewire tube, communicate with the interior 96 of the guidewire tube. The channel 120 thus supplies the guidewire tube interior 96 and hence the secondary balloon with hydraulic fluid.

The O-rings 112 and 113 impart adjustability to the connections between the elements. The first O-ring 112 serves to separate the two hydraulic systems and to prevent fluid loss from both the distal reservoir 119 and the primary balloon supply lumen 24. The second O-ring 113 serves to retain fluid within the confines of the system and to prevent fluid loss from the proximal reservoir 121 and the secondary balloon supply lumen 96. Both O-rings 112, 113 may be adjusted to permit rotational mobility of the guidewire tube 101 relative to the stationary elements 108, 109, and 110 while preventing both (1) fluid flow between the reservoirs or out the proximal end of the system and (2) axial mobility of the guidewire assembly as a whole relative to the catheter component of the system. For convenience of use, the system is preferably supplied for use in a condition in which with the two O-rings 112, 113 have been pre-adjusted to permit rotation of the guidewire assembly relative to the catheter component while preventing fluid flow and relative axial mobility.

The rotator 111 is constructed in three parts—two longitudinally disposed rotational elements 131, 132, and a pin-vise 133 similar to the pin-vise 83 of FIG. 6. By virtue of an interlocking rotational connection 134, the rotator is rotatable relative to the stationary elements 108, 109, and 110. The rotational elements 131, 132 themselves are joined by a threaded connection 134 which is either a left-hand or right-hand thread. By rotating the most distal of the two rotational elements 131 either clockwise or counterclockwise relative to the proximal rotational element 132, one may either release the pin-vise 133 from the guidewire tube 101, or seize the tube with the pin-vise to facilitate axial movement or rotational movement of the guidewire assembly relative to the catheter component of the system.

The guidewire assembly may be withdrawn from a vasculature while leaving the catheter component in place, by first deflating both balloons 13, 94 and releasing the pressure on both O-rings 112, 113 and the pin-vise 133. Release of the O-rings 112 and 113 is achieved by rotating the adjacent stationary elements 108, 109 and 109, 110, respectively, relative to each other. Release of the pin-vise 133 is achieved by rotating the components of the rotator 131, 132 relative to each other. This renders the guidewire assembly movable relative to the catheter component. The guidewire assembly is then drawn out, and another guidewire assembly can inserted in its place and advanced through the system. At the distal end of the system, the tapering proximal ends 32 of the indentations 29 which serve as a mounting for the column support tube 14 will direct the new guidewire into the column support tube, in the same manner as discussed above in connection with FIG. 3.

Withdrawal of the catheter component from the guidewire component requires first extending the guidewire component by attaching a guidewire extension, an example of which is illustrated in FIGS. 11A, 11B, 11C and 11D, discussed below, deflating both balloons 13, 94, and then releasing components 104, 111 and 118 as above. To permit the attachment of a guidewire extension, the guidewire tube is closed at its proximal end by a short length of rod 130. The function of this short length of rod in the attachment of the extension is explained fully below. This technique enables one to withdraw of the catheter component from the guidewire component without sacrificing intra-luminal access.

FIG. 9A depicts a system which includes an inflatable seizing member and in which all of the following can be performed:

(1) the catheter body can be exchanged independently of the guidewire assembly;
(2) the guidewire assembly can be exchanged independently of the catheter body;
(3) either balloon can be advanced or retracted relative to the other and inflated and deflated independently of the other over a range of axial displacements of one balloon relative to the other;
(4) either balloon can be used for dilatation purposes with both components inserted in a body vessel; and
(5) the secondary balloon on the guidewire assembly can seize the catheter body at any position along the length of the catheter body from the distal end to the proximal end.

The FIG. 9A system is identical to that of FIG. 8 in the construction of the shaft and the distal end of the system, and for this reason, the shaft and distal end are not shown. The difference lies at the proximal end, where the proximal adapter includes an added section 141 intervening between the two elements 142, 143 which correspond to the two most distal stationary elements 108, 109 of the proximal adapter of FIG. 8. The added section 141 is in two halves 144, 145, the distal half 145 joined to the neighboring element on the distal side 142 by a screw connection 146 with an O-ring 147 in between, and the proximal half 144 joined to the neighboring element on the proximal side 142, likewise by a screw connection 148 with an O-ring 149 in between. The two halves have complementary facing ends, one male 150 and one female 151 which are readily joined and pulled apart. The O-rings 147 and 149 serve to contain the hydraulic fluid in either of the two reservoirs 152, 153 so that leakage is prevented regardless of the degree of separation of the two halves of the added section. The remaining O-ring 154 and the pin-vise 155 are counterparts of and identical to the corresponding O-ring 113 and pin-vise 135 of FIG. 8, and the three most proximal sections 156, 157 and 158 of the adapter are counterparts of and identical to the corresponding sections 110, 131 and 132 of FIG. 8.

To exchange the catheter body, a guidewire extension is first attached to the proximal end 158 of the guidewire, then all three O-rings 147, 149 and 154 and the pin-vise 155 are loosened. All parts of the proximal adapter are then removed as a unit by grasping the distal segment 142 and pulling in the proximal direction. To exchange the guidewire assembly, at least one among the two proximal O-rings 149, 154 is left in the tightened state over the guidewire tube, and the proximal half 144 of the added section of the adapter is pulled in the proximal direction, taking with it all of the sections 143, 155, 156 and 157 which are proximal to it.

FIG. 9B illustrates the guidewire assembly included in the combination shown in FIG. 9A, in full length profile view. This guidewire assembly can be installed alone within the vasculature and used to dilate lesions independently of the catheter component shown in FIG. 9A. In the event that an exchange procedure is required when this guidewire assembly is used alone, the assembly can be extended and the proximal adapter removed as previously described. One may then introduce an over-the-wire catheter by passing it over the length of the extended guidewire assembly and across the confines of the lesion requiring treatment. Note that this also is done without the need to sacrifice intraluminal access.

FIG. 10 illustrates how the balloon of a conventional balloon-on-a-wire device may be used as the seizing mechanism of the present invention by insertion of the balloon-on-a-wire device inside an over-the-wire catheter, using the balloon-on-a-wire device as the guidewire. The balloon-on-a-wire device consists of a tubular shaft 161 which has proximal and distal segments differing in flexibility in the same manner as the guidewire tube of FIG. 8, a highly flexible wire-coil tip 162, a cylindrical balloon 163, and a supporting guidewire 164 permanently mounted by bonds at both ends of the guidewire to the inside of the tubular shaft and the inside of the flexible tip, respectively. The proximal end 165 of the tubular shaft is open for access to the shaft interior to supply hydraulic fluid to the balloon 163, and a fitting 166 is mounted over its outer surface to permit connection with a hydraulic fluid supply source.

The over-the-wire catheter through which the balloon-on-a-wire device is inserted has a catheter body and distal end identical to that of FIGS. 1A and 1B, but with a simpler proximal adapter 167. The proximal adapter contains but a single reservoir 168, a single side arm 169 and a single O-ring 170. The O-ring 170 seals the hydraulic regions of the catheter body, and can be tightened or loosened to prevent or permit one to advance or retract the internal balloon-on-a-wire device relative to the external catheter body. The balloon 163 of the internal balloon-on-a-wire device can either be advanced far enough to protrude from the distal end of the outer catheter body and thus be useful for dilatation, or it may be retracted as shown to seize the outer catheter body when inflated. Seizure may be achieved at any location within the outer catheter body, either on the internal surface of the column support tube 171 or on the internal surface of the catheter body shaft 172. Sequential seizure at periodically spaced locations within the outer catheter body progressing toward the proximal end of the outer catheter body is in certain applications a useful means of advancing the outer catheter body through a particularly tortuous bodily vessel.

FIG. 10 is but one example of the combination of a balloon-on-a-wire device with an over-the-wire catheter body. A wide range of both balloon-on-a-wire devices and over-the-wire devices known to those skilled in the art, and likewise a variety of combinations, can be used in this aspect of the invention. An advantage of the combination shown in FIG. 10, however, where the outer catheter body is a single-channel device, is that there is a high degree of clearance around the internal balloon-on-a-wire device to promote rapid hydraulic fluid flow to and from the primary balloon, and that the outer diameter of the outer catheter body can be relatively small while still providing high clearance for hydraulic fluid flow.

The combination depicted in FIG. 10 offers several advantages over devices with balloon-on-a-wire construction alone as well as devices which combine balloon-on-a-wire construction with conventional over-the-wire construction which is multi-lumen for the entire length of the catheter. When compared to simple balloon-on-a-wire devices, the combination depicted in FIG. 10 offers the advantage of the ability to exchange one balloon-on-a-wire device for another without removing the outer catheter body from the vasculature, and thus without sacrificing intra-luminal access. When compared to the combination of a conventional balloon-on-a-wire device and a conventional multi-lumen over-the-wire device, the FIG. 10 combination offers a superior combination of larger hydraulic channel and smaller external shaft profile. These features provide the FIG. 10 combination with superior hydraulic performance, i.e., more rapid balloon inflation and deflation rates, and greater clearance around the exterior of the over-the-wire catheter body which results in a diminished propensity of the system to interfere with the flow of medications, contrast media and blood through the vasculature in the regions surrounding the catheter body.

The combination of FIG. 10 does not permit the withdrawal of the over-the-wire catheter component over the balloon-on-a-wire device in the same manner as the system of FIG. 8, however. To accomplish a catheter exchange with the combination of FIG. 10, the balloon-on-a-wire device is first exchanged for either an extendable wire or an exchange wire. The catheter component is then withdrawn from the newly inserted guidewire component, and the substitute catheter may then be introduced over the guidewire and into the vasculature.

The guidewire extension is essentially an additional guidewire of a length exceeding that of the guidewire already inside the catheter body. The connection between the two guidewires may be any of a wire variety of structures which will provide a smooth transition between the guidewires such that the catheter body and the proximal adapter can be easily drawn over the connection.

FIGS. 11A, 11B, 11C and 11D illustrate one example of a guidewire extension and coupling mechanism. An advantage of this particular mechanism is that coupling is achieved without the use of a compressive force which might result in the formation of kinks in the guidewire. FIGS. 11A and 11C show the extension and coupling mechanism in cross section. FIGS. 11B and 11D show the elements of FIGS. 11A and 11C, respectively, in perspective.

Figure 9:
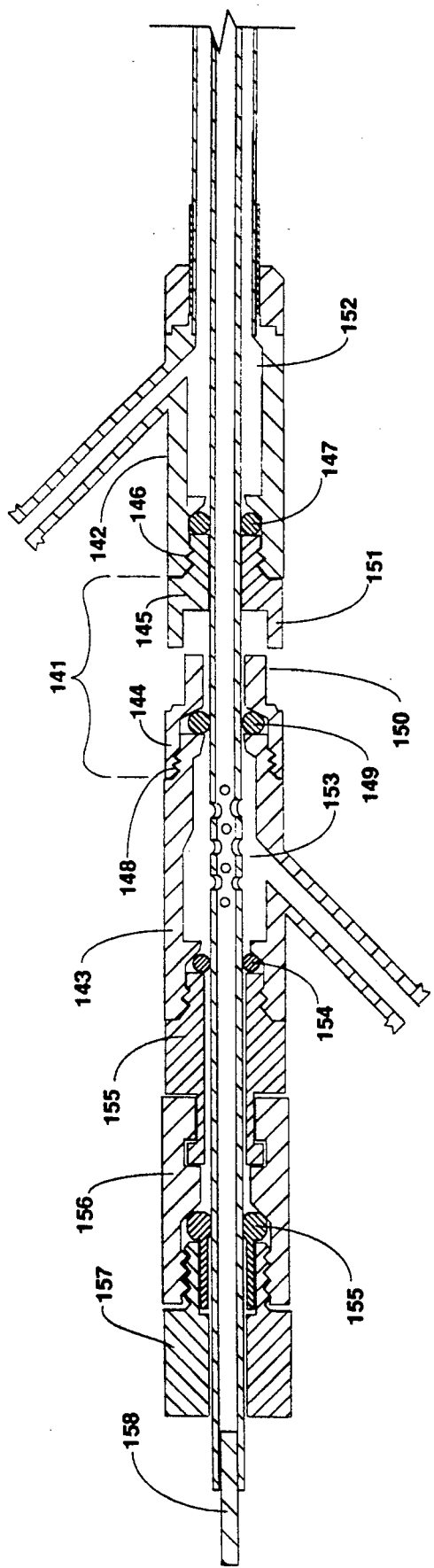
FIGS. 9A and 9B illustrate a sixth embodiment of the invention, in a cross-section views.

The extension mechanism shown in these Figures consists of:

(1) a reduced diameter segment 171 at the proximal end of the original guidewire rod 16—for guidewire assemblies of the type depicted in FIGS. 8 and 9, this reduced diameter segment will be the proximal tip of the short length of rod 130 (FIG. 8) or 158 (FIG. 9) extending from the proximal end of the guidewire tube;

(2) a tubular element 172 affixed to the distal end of the extension wire 173 over a reduced diameter segment 174, the distal portion of the tubular element containing longitudinal slots 175 which when separated as shown in FIG. 10B expand the tubular element sufficiently to permit insertion of the reduced diameter segment 171 of the guidewire; and (3) a sleeve 176 surrounding the tubular element 172 in a slidable manner.

Coupling the extension wire 173 to the guidewire assembly is accomplished by inserting the reduced diameter segment 171 at the proximal end of the guidewire inside the tubular element 172 while the sleeve 176 is in the retracted position shown in FIGS. 11A and 11B. The sleeve is then slid toward the guidewire (in the direction indicated by the arrow 177) to cover the slotted portion of the tubular element, whereupon the sleeve compresses the slotted portion to close the slots and force the slotted portion snugly over the reduced diameter section 171. This joins the parts together in a secure manner without any compressive force and thus with little if any risk of kink formation in the guidewire. Additional mechanisms for coupling a guidewire extension, which may also be used, are disclosed in co-pending United States patent application Ser. No. 07/813,337, filed Dec. 23, 1991, entitled "Guidewire Extension Mechanism," inventor Jeff L. Kraus.

The various components and elements of these embodiments of the invention may be made from conventional materials, many of which are in current use in catheter construction. As for the deformable section in its various forms, a particularly convenient material is a urethane-nylon type composition such as Pebax, manufactured by Atochem, Inc., of Glen Rock N.J., U.S.A. A convenient material for hollow guidewire tubes is stainless steel hypodermic needle tubing such as that which is sold under the trademark HYPOTUBE of Popper and Sons, New Hyde Park, N.Y., U.S.A.

The following is a description of the operation of a catheter-guidewire system in accordance with this invention, utilizing one of the embodiments which provides unrestricted guidewire rotational mobility while the guidewire and the catheter component are in the seized (and thus fluid-tight) condition by virtue of the seizing member.

Initially, both catheter and guidewire, in the seized condition, are introduced as a single unit into the body vessel. In this condition, the combined components operate in a manner analogous to that of a fixed-wire device. Directional control of the system is achieved by rotation of the guidewire during advancement within the body vessel, utilizing the curve at the distal tip of the guidewire to direct the system through the vasculature. With the guidewire and the catheter body seized in this manner, the two components are joined at both the proximal and distal ends of the guidewire, which permits the guidewire to add its own column strength to the column strength inherent in the catheter body. This enhances the pushability of the system and thereby facilitates the introduction of the balloon component of the system across the confines of a stenosis sought to be dilated. In the event that the catheter balloon cannot be advanced across the stenosis, the guidewire and the catheter components are disengaged by relaxing the seizing member and adjusting the proximal adapter to disconnect the components at their distal and proximal ends, respectively. The guidewire component may then be advanced relative to and independently of the catheter component. In many cases, once the guidewire alone has passed the stenosis, the catheter component and hence the catheter balloon can then be more easily advanced across the stenosis as well.

For those embodiments in which the seizing member also serves as a fluid seal, the seizing member must be engaged to render the system fluid tight either before or after the balloon is in position and before the balloon is inflated. Engagement of the seizing member is accomplished either by retracting one element of the guidewire assembly relative to the other or by infusion of fluid into the guidewire, depending on whether the seizing member is an axially collapsible tube or a secondary balloon. If it is necessary to exchange the catheter component without withdrawing the guidewire component (i.e., without sacrificing intraluminal access), this is accomplished by disengaging the guidewire component from the catheter component both proximally and distally as described above, coupling a guidewire extension to the guidewire component, and withdrawing the catheter component over the extended guidewire component. If it is necessary to exchange the guidewire component without withdrawing the catheter component, this is accomplished by again disengaging the guidewire component from the catheter component both proximally and distally, followed by withdrawing the guidewire component relative to the catheter component.

A balloon catheter-guidewire system which is single-channel for most of its length and which contains both primary and secondary balloons, may be used in a sequential dilatation in accordance with this invention procedure as follows.

With the secondary balloon inflated and thus seizing the guidewire to the catheter, the system is advanced in the same way that a fixed-wire device would be advanced, to the vicinity of the lesion requiring treatment. In this condition, the guidewire contributes to the pushability of the system, thereby facilitating the advancement of the system through the vasculature and across the stenosis. If the stenosis is such that the primary balloon cannot be advanced across it, the guidewire is released from the catheter both proximally and distally, by releasing the appropriate O-ring(s) and deflating the secondary balloon. Thereafter, the guidewire is advanced relative to the catheter component to cause the secondary balloon to emerge from the distal end of the catheter component, and advancement is continued until the secondary balloon is in position across the stenosis. With its lower crossing profile, the secondary balloon can be advanced through stenoses that cannot be penetrated by the primary balloon. Once in position, the secondary balloon is inflated to dilate the stenosis to a sufficient degree that the primary balloon can pass through. The secondary balloon is then withdrawn to the interior of the support tube inside the catheter component. Once the secondary balloon is positioned within the support tube, the appropriate O-rings are tightened and the secondary balloon is again inflated. This will cause the secondary balloon to both seize the guidewire to the catheter and seal the hydraulic channel which is continuous with the primary balloon. The system is then advanced in this condition across the stenosis in the manner of a fixed-wire device, and the primary balloon is then used to complete the dilatation. In the event that an exchange procedure is then required, either the catheter or guidewire can be withdrawn independently of the other component of the system, in accordance with the techniques previously described, enabling the exchange to be made without the need to sacrifice intraluminal access.

The following is a description of the independent operation in accordance with this invention of a guidewire assembly containing a dilatation balloon and guidewire extension. The assembly is advanced in the deflated condition across a region of stenosis and, once there, inflated to dilate the lesion requiring treatment. If an exchange procedure is required, the proximal adapter of the guidewire is removed by loosening the appropriate O-rings, and the guidewire is extended to permit the introduction of a second catheter over the length of the extended guidewire while the guidewire balloon is in the deflated state. This approach enables one to perform a balloon dilatation with a particular low profile device, and to perform a catheter exchange without the need to sacrifice intraluminal access during this process.

Catheter systems with guidewire assemblies in accordance with this invention can be purged of air and filled with inflation media by conventional procedures, although the guidewire assembly permits one to use a more convenient procedure, as follows. With the guidewire assembly fully inserted in the catheter body and the seizing member in a relaxed condition (not in engagement with the catheter body), inflation media is injected into the inflation port in the proximal adapter. Injection of inflation media is continued until media begins to leak from the distal tip of the catheter. This process will fill the shaft of the catheter with inflation media and simultaneously purge the shaft of air. Once the shaft is filled and purged of air, the seizing member on the guidewire assembly is then deformed to seize and seal the catheter body, and the system is ready for use.

Although filled with inflation media, the dilatation balloon on the catheter body must be in the deflated condition before the system can be advanced into a vasculature. This is accomplished in a variety of ways. For example, a vacuum may be pulled on the system after the seizing member has been deformed, thereby collapsing the balloon without admitting air back in. Alternatively, the entire injection and venting procedure may be performed with a restricting sheath around the dilatation balloon to prevent inflation of the balloon. Dilatation balloon catheters are generally supplied with the balloon encased in a removable protective sheath of this nature which serves this purpose well. Once venting is completed, the sheath is removed and the system is ready for use.

These are but examples of the various ways that systems in accordance with this invention can be manipulated, and of the various functions that these systems can perform.

The foregoing descriptions are offered primarily for purposes of illustration. It will be readily apparent to those skilled in the art that the construction of the system, the materials, the type, arrangement and location of components, and other parameters of the system may be further modified or substituted in various ways without departing from the spirit and scope of the invention.

What is claimed is:

1. A guidewire assembly for insertion in a catheter lumen extending longitudinally inside a catheter for purposes of mediating the advancement of said catheter through a bodily vessel, said catheter lumen having an internal wall surface, said guidewire assembly comprising:
   an outer surface, a portion of which is formed by a length of axially collapsible tubing which, when compressed axially, gathers into folds which bulge sufficiently to seize said internal wall surface of said catheter lumen and thereby join said catheter to said guidewire assembly, and
   compression means engaging said portion of said outer surface for so compressing said length of axially collapsible tubing.

2. A guidewire assembly in accordance with claim 1 further comprising an outer tubular component defining a guidewire internal lumen and an inner component extending through said guidewire internal lumen, said length of axially collapsible tubing being a portion of said outer tubular component, and said outer tubular component and said inner component being capable of axial movement relative to each other, said axial movement causing said deformable section to bulge sufficiently to seize said internal wall surface of said catheter lumen and thereby join said catheter to said guidewire assembly.

3. A guidewire assembly in accordance with claim 2 further comprising means for locking said outer tubular component and said inner component against movement relative to each other.

4. A guidewire assembly in accordance with claim 1 in which said guidewire assembly has proximal and distal ends, with a tip secure to said distal end, said tip being of substantially greater flexibility than the remainder of said guidewire assembly.

5. A guidewire assembly in accordance with claim 2 in which said guidewire assembly has proximal and distal ends, with a tip secured to said distal end, said tip being a coil of substantially greater flexibility than the remainder of said guidewire assembly, and said inner component secured to said tip.

6. A guidewire assembly in accordance with claims 1, 2, 3, 4 or 5 in which said guidewire assembly has proximal and distal ends, with a flexible coil tip secured to said distal end, and said length of axially collapsible tubing is at said distal end.

7. A guidewire assembly in accordance with claim 1 in which said guidewire assembly has proximal and distal ends, said length of axially collapsible tubing is at said distal end, and said guidewire assembly further comprises actuating means at said proximal end for actuating said compression means.

8. A guidewire assembly in accordance with claim 2 in which said guidewire assembly has proximal and distal ends, with a flexible coil tip secured to said distal end, said length of axially collapsible tubing is at said distal end, said inner component is a rod secured to said length of axially collapsible tubing at a distal end thereof and to said flexible coil tip.

9. A guidewire assembly in accordance with claim 2 in which said outer tubular component and said inner component are capable of unrestricted rotation relative to each other irrespective of said axial movement.

10. A guidewire assembly in accordance with claim 2 in which:
   said guidewire assembly has proximal and distal ends, with a flexible coil tip secured to said distal end,
   said length of axially collapsible tubing is at said distal end,
   said inner component is a rod secured to said flexible coil tip, and
   said rod and outer tubular member are engaged by engaging means comprised of a first engaging member on said rod and a second engaging member on said outer tubular member, one of said engaging members being a protrusion and the other an indentation, such that when said engaging members are engaged, said rod and said outer tubular member are mobile rotationally but not longitudinally relative to each other.

11. A guidewire assembly in accordance with claim 10 in which said first engaging member is a circumferential groove and said second engaging member is a circumferential flange small enough to be received inside said groove.

12. A guidewire assembly in accordance with claim 1 in which said guidewire assembly has proximal and distal ends, with a flexible tip secured to said distal end, said tip being of substantially greater flexibility than the remainder of said guidewire assembly, and said guidewire assembly further comprises:
    an outer tubular component defining a guidewire internal lumen, said length of axially collapsible tubing being a distal portion of said outer tubular component,
    an actuating component axially movable relative to said outer tubular component to cause said axially collapsible tubing to bulge sufficiently to seize said internal wall surface of said catheter lumen and thereby join said catheter to said guidewire assembly, and
    an inner component extending through said guidewire internal lumen and terminating in said flexible tip, said inner component independently rotatable relative to said outer tubular component and said actuating component irrespective of axial movement of said actuating component.

13. A guidewire assembly in accordance with claim 12 in which said flexible tip is a coil.

14. A guidewire assembly in accordance with claim 12 further comprising means for locking said actuating component and said outer tubular member against movement relative to each other.

15. A guidewire assembly in accordance with claim 1 in which said guidewire assembly has distal and proximal ends and further comprises a fixture removably attached to said proximal end, said fixture containing said compression means.

16. A guidewire assembly in accordance with claim 1 in which said guidewire assembly has distal and proximal ends, and said proximal end includes means for attachment of a guidewire extension to permit withdrawal of said catheter over said guidewire assembly without removing said guidewire assembly from said bodily vessel.

17. A guidewire assembly in accordance with claim 1 in which said compression means is reversible to permit release of said catheter from said guidewire assembly once joined.

18. A composite catheter/guidewire system comprising:
    a catheter body comprised of a shaft, an inflatable balloon at a distal end of said shaft, an inner tubular member having an interior wall surface, said inner tubular member being substantially shorter than said shaft and mounted inside said catheter body in such a manner as to maintain elongation of said inflatable balloon;
    a guidewire assembly within said inner tubular member, said guidewire assembly comprising:
        an outer surface, a portion of which is a deformable section which deforms to seize said interior wall surface of said inner tubular member and thereby join said catheter body to said guidewire assembly; and
        deformation means for so deforming said deformable section.

19. A composite catheter/guidewire system in accordance with claim 18 in which said deformable section upon deformation seals said inner tubular member against the passage of fluid therethrough while permitting fluid communication between said shaft and said inflatable balloon.

20. A composite catheter/guidewire system in accordance with claim 18 in which said guidewire assembly has proximal and distal ends, with a tip of substantially greater flexibility than the remainder of said guidewire assembly secured to said distal end.

21. A composite catheter/guidewire system in accordance with claim 18 in which said guidewire assembly has proximal and distal ends, and said deformable section is at said distal end.

22. A composite catheter/guidewire system in accordance with claim 18 in which said guidewire assembly has proximal and distal ends, said deformable section is at said distal end, and said deformation means is actuatable at said proximal end.

23. A composite catheter/guidewire system in accordance with claim 18 in which said deformable section is a length of axially collapsible tubing which, when compressed axially, gathers into folds which bulge sufficiently to seize said interior wall surface of said inner tubular member.

24. A composite catheter/guidewire system in accordance with claim 23 in which said guidewire assembly further comprises an outer tubular component, and intermediate tubular component and an inner elongate component, all coaxial, said length of axially collapsible tubing being a portion of said outer tubular component, and said outer tubular component and said intermediate tubular component being capable of axial movement relative to each other, said axial movement causing said deformable section to bulge sufficiently to seize said internal wall surface of said catheter lumen and thereby join said catheter to said guidewire assembly.

25. A composite catheter/guidewire system in accordance with claim 18 in which said guidewire assembly further comprises an outer tubular component defining a guidewire internal lumen and an inner component extending through said guidewire internal lumen, a length of axially collapsible tubing being a portion of said outer tubular component, and said outer tubular component and said inner component being capable of axial movement relative to each other, said axial movement causing said deformable section to bulge sufficiently to seize said internal wall surface of said catheter body and thereby join said catheter to said guidewire assembly.

26. A composite catheter/guidewire system in accordance with claim 25 further comprising means for locking said outer tubular component and said inner component against movement relative to each other.

27. A composite catheter/guidewire system in accordance with claim 25 in which said outer tubular component and said inner component are engaged in a manner permitting said axial movement and further permitting unrestricted rotation relative to each other irrespective of said axial movement.

28. A composite catheter/guidewire system in accordance with claim 27 in which said outer tubular component and said inner component are engaged by a first engaging member on said outer tubular component and a second engaging member on said inner component, one of said engaging members being a circumferential groove and the other a circumferential flange small enough to be received inside said groove.

29. A composite catheter/guidewire system in accordance with claim 25 in which said guidewire assembly has proximal and distal ends, said guidewire assembly further comprising a locking means at said proximal end for locking said inner component relative to said outer tubular component.

30. A composite catheter/guidewire system in accordance with claim 29 further comprising a fixture removably attached to said guidewire assembly at said proximal end, said fixture containing said locking means.

* * * * *